United States Patent [19]
Miller et al.

[11] Patent Number: 6,124,329
[45] Date of Patent: Sep. 26, 2000

[54] METALLOPROTEINASE INHIBITORS

[75] Inventors: Andrew Miller; Mark Whittaker; Raymond Paul Beckett, all of Oxford, United Kingdom

[73] Assignee: British Biotech Pharmaceuticals Ltd., United Kingdom

[21] Appl. No.: 09/343,087

[22] Filed: Jun. 30, 1999

Related U.S. Application Data

[62] Division of application No. 08/765,140, filed as application No. PCT/GB95/01464, Jun. 22, 1995, Pat. No. 5,962,529.

[30] Foreign Application Priority Data

Jun. 22, 1994 [GB] United Kingdom ................... 9412514
Mar. 24, 1995 [GB] United Kingdom ................... 9506107

[51] Int. Cl.$^7$ ......................... A61K 31/41; C07D 285/06
[52] U.S. Cl. ....................... 514/361; 514/238.2; 514/507; 514/541; 544/169; 548/127; 560/13; 560/312
[58] Field of Search ................... 514/575, 542, 514/563, 576, 507, 361, 541, 238.2; 560/312, 13; 554/50; 548/127; 544/169

[56] References Cited

U.S. PATENT DOCUMENTS

| | | |
|---|---|---|
| 4,885,027 | 12/1989 | Pomidor . |
| 5,300,501 | 4/1994 | Porter et al. . |
| 5,310,763 | 5/1994 | Campion et al. . |
| 5,552,419 | 9/1996 | MacPherson et al. . |
| 5,817,822 | 10/1998 | Nantermet et al. ..................... 546/194 |
| 5,962,529 | 10/1999 | Miller et al. ............................ 514/575 |

*Primary Examiner*—Shailendra Kumar
*Attorney, Agent, or Firm*—Banner & Witcoff, Ltd.

[57] ABSTRACT

Compounds of general formula (II)

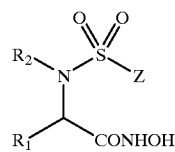

(II)

wherein $R_1$, $R_2$ and Z are defined in the claims, are matrix metalloproteinase inhibitors.

10 Claims, No Drawings

METALLOPROTEINASE INHIBITORS

This application is a Division of Ser. No. 08/765,140, filed Dec. 23, 1996, now U.S. Pat. No. 5,962,529 which is a 371 of PCT/GB95/01464, filed Jun. 22, 1995.

The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteinases involved in tissue degradation.

BACKGROUND TO THE INVENTION

Metalloproteinase Inhibitors

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas.

Metalloproteinases are characterised by the presence in the structure of a zinc(II) ion at the active site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (L. M. Matrisian, *Trends in Genetics,* 1990, 6, 121–125).

Many known MMP inhibitors are peptide derivatives, based on naturally occurring amino acids, and are analogues of the cleavage site in the collagen molecule. A recent paper by Chapman et al (J. Med. Chem. 1993, 36, 4293–4301 ) reports some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the zinc (II) site in the MMP, and known classes include those in which the zinc binding group is a hydroxamic acid, carboxylic acid, sulphydryl, and oxygenated phosphorus (eg phosphinic acid and phosphonic acid) groups.

Two known classes of pseudopeptide or peptide mimetic MMP inhibitors have a hydroxamic acid group and a carboxylic group respectively as their zinc binding groups. With a few exceptions, such known MMPs may be represented by the structural formula (IA)

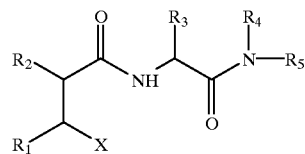

(IA)

in which X is the zinc binding hydroxamic acid (—CONHOH) or carboxylic acid (—COOH) group and the groups $R_1$ to $R_5$ are variable in accordance with the specific prior art disclosures of such compounds. The following patent publications disclose hydroxamic acid-based and/or carboxylic acid-based MMP inhibitors:

| | |
|---|---|
| US 4599361 | (Searle) |
| EP-A-2321081 | (ICI) |
| EP-A-0236872 | (Roche) |
| EP-A-0274453 | (Bellon) |
| WO 90/05716 | (British Bio-technology) |
| WO 90/05719 | (British Bio-technology) |
| WO 91/02716 | (British Bio-technology) |
| WO 92/09563 | (Glycomed) |
| US 5183900 | (Glycomed) |
| US 5270326 | (Glycomed) |
| WO 92/17460 | (SmithKline Beecham) |
| EP-A-0489577 | (Celltech) |
| EP-A-0489579 | (Celltech) |
| EP-A-0497192 | (Roche) |
| US 5256657 | (Sterling Winthrop) |
| WO 92/13831 | (British Bio-technology) |
| WO 92/22523 | (Research Corporation Technologies) |
| WO 93/09090 | (Yamanouchi) |
| WO 93/09097 | (Sankyo) |
| WO 93/20047 | (British Bio-technology) |
| WO 93/24449 | (Celltech) |
| WO 93/24475 | (Celltech) |
| EP-A-0574758 | (Roche) |
| WO 94102447 | (British Biotech) |
| WO 94/02446 | (British Biotech) |

BRIEF DESCRIPTION OF THE INVENTION

The present invention makes available a new class of MMP inhibitors, related to those of general formula (I) known from the patent publications listed above in that they also have hydroxamic acid or carboxylic acid zinc binding groups, but incorporating a major structural change in the "backbone". In the compounds of this invention the portion of the "backbone" corresponding to the bracketed portion of general formula (I) may be represented by partial formula (IIA):

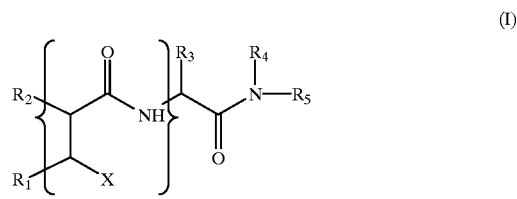

(I)

-continued

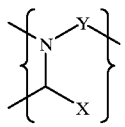

(IIA)

where Y is a carbonyl (—C(=O)—) or sulphonyl (—S(=O)$_2$—) group.

A further advantage of compounds of the present invention is that they inhibit the production of the pro-inflammatory cytokine TNF.

RELATED PATENT PUBLICATION

EP-A-0606046 (Ciba-Geigy), published Jul. 13, 1994 discloses compounds also having the partial structure (IIA) where Y is a sulphonyl group.

DETAILED DESCRIPTION OF THE INVENTION

The present invention provides a compound of general formula (II)

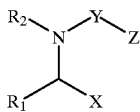

(II)

wherein

X represents a —CO$_2$H or —CONHOH group;

$R_1$ represents the characterising side chain of a natural or non-natural alpha amino acid, in which any functional group present may be protected;

$R_2$ represents (i) a group $Z^1$—Q—W—, or (ii) ($Z^1$—U—W—)$_2$CH— in which each of the two groups $Z^1$—Q—W— present may be the same or different, and wherein in both cases (i) and (ii):

$Z^1$ represents hydrogen or an optionally substituted aryl, heteroaryl, non-aromatic heterocyclyl, cycloalkyl, or cycloalkenyl group, and —Q—W— taken together represent a bond, or Q represents a bond or —O— or —S— and W represents a divalent $C_1$–$C_{20}$ straight or branched alkyl or $C_2$–$C_{20}$ alkenyl group which (a) may be interrupted by one or more non-adjacent ether or thioether linkages or —N($R_x$)— groups wherein $R_x$ is hydrogen, or $C_1$–$C_6$ alkyl, and/or (b) may carry one or more substituents selected from —OH, —SH, —O(Alk), —S(Alk), halogen, —NH$_2$, —NH(Alk), —N(Alk)$_2$, —CO$_2$H, —CO$_2$(Alk), —CO(Alk), —CHO, —CONH$_2$, —CONH(Alk), —CON(Alk)$_2$, —(Alk)OH, —(Alk)SH, and —NHCO(Alk) where Alk represents $C_1$–$C_6$ alkyl;

Y represents a carbonyl (—C(=O)—) or sulphonyl (—(SO$_2$)—) group;

Z represents (A) a group $R_2$ as defined above PROVIDED THAT when Y is a sulphonyl group then Z is not an aryl or heteroaryl group, or (B) a group of formula (III)

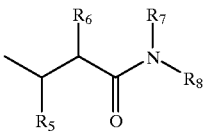

(III)

wherein $R_5$ represents hydrogen or ($C_1$–$C_6$)alkyl;

$R_6$ represents the characterising side chain of a natural or non-natural alpha amino acid, in which any functional group present may be protected;

$R_7$ is hydrogen, $C_1$–$C_6$ alkyl, ($C_1$–$C_4$)perfluoroalkyl; or a group D-($C_1$–$C_6$)alkyl wherein D represents hydroxy, ($C_1$–$C_6$)alkoxy, ($C_1$–$C_6$)alkylthio, acylamino, optionally substituted phenyl or heteroaryl, NH$_2$, or mono- or di-($C_1$–$C_6$)alkylamino; or a phenyl group, which may be optionally fused to a benzene ring or to a heterocyclic ring, and wherein any of the rings may be optionally substituted; or a heterocyclic ring, which heterocyclic ring may be optionally fused to a benzene ring or to a further heterocyclic ring, and wherein any of the rings may be optionally substituted;

$R_8$ is hydrogen or a ($C_1$–$C_6$)alkyl group;

or a salt, hydrate or solvate thereof.

A particular sub-set of the compounds of the present invention are those of formula (II) above wherein $R_2$ represents (i) a group Ar—Q—W— in which Ar represents optionally substituted aryl or heteroaryl, Q represents a bond or —O— or S—, and W represents a divalent $C_1$–$C_{20}$ straight or branched chain alkyl moiety which may carry one or more substituents selected from OH, OMe, halogen, NH$_2$, NMeH, NMe$_2$, CO$_2$H, CO$_2$Me, COMe, CHO, CONH$_2$, CONHMe, CONMe$_2$, CH$_2$OH, NHCOMe;

(ii) heterocyclyl($C_1$–$C_6$)alkyl, cycloalkyl ($C_1$–$C_6$)alkyl or cycloalkenyl($C_1$–$C_6$)alkyl group; or (iii) a linear saturated or unsaturated $C_2$–$C_{20}$ hydrocarbon chain, which chain (a) may be interrupted by one or more non-adjacent —O— or —S— atoms or —N($R_x$)— groups wherein $R_x$ is hydrogen, methyl or ethyl, and/or (b) may be substituted with one or more groups selected from ($C_1$–$C_6$)alkyl, OH, OMe, halogen, NH$_2$, NMeH, NMe$_2$, CO$_2$H, CO$_2$Me, COMe, CHO, CONH$_2$, CONHMe, CONMe$_2$, CH$_2$OH, NHCOMe, provided that the maximum length of the chain is no more than 28 C, O, S and N atoms; and Z represents:

(A) an optionally substituted ($C_3$–$C_8$)cycloalkyl, ($C_4$–$C_8$) non-aromatic cycloalkenyl, or 5 to 8 membered non-aromatic heterocyclic group, which groups may be optionally fused to a benzene ring or to a heterocyclic ring; or (B) a group of formula —CHR$_3$R$_4$ wherein $R_3$ and $R_4$ separately represent hydrogen; or an optionally substituted aryl, heteroaryl, ($C_3$–$C_8$) cycloalkyl, ($C_4$–$C_8$)non-aromatic cycloalkenyl, or 5 to 8 membered non-aromatic heterocyclic group; or a group —[Alk]$_n$R$_a$ where Alk is an optionally substituted ($C_1$–$C_6$)alkyl or ($C_2$–$C_6$)alkenyl group optionally interrupted by one or more non-adjacent —O—, or —S— atoms or —N(R$_b$)-groups [where R$_b$ is a hydrogen atom or a $(C_1-C_6)$alkyl group], n is 0 or 1, and $R_a$ is (i) hydrogen or (ii) an optionally substituted $(C_1-C_{17})$alkyl, $(C_2-C_{17})$alkenyl or $(C_2-C_{17})$ alkynyl group optionally interrupted by one or more non-adjacent —O—, or —S— atoms or —N($R_b$)- groups [where $R_b$ is a hydrogen atom or a $(C_1-C_6)$ alkyl group] or (iii) an optionally substituted aryl, heteroaryl, $(C_3-C_8)$cycloalkyl, $(C_4-C_8)$non-aromatic cycloalkenyl, or 5 to 8 membered non-aromatic heterocyclic group;

A further particular sub-set of the compounds of the present invention are those of formula (II) above wherein $R_2$ represents a phenyl$(C_1-C_6)$alkyl, heterocyclyl$(C_1-C_6)$ alkyl, cycloalkyl $(C_1-C_6)$alkyl or cycloalkenyl$(C_1-C_6)$ alkyl group, or a linear saturated or unsaturated $C_2-C_{20}$ hydrocarbon chain, which chain (a) may be interrupted by one or more non-adjacent —O— or —S— atoms or —N($R_x$)— groups wherein $R_x$ is hydrogen, methyl or ethyl, and/or (b) may be substituted with one or more groups selected from $(C_1-C_6)$alkyl, OH, OMe, halogen, $NH_2$, NMeH, $NMe_2$, $CO_2H$, $CO_2Me$, COMe, CHO, $CONH_2$, CONHMe, $CONMe_2$, $CH_2OH$, NHCOMe, provided that the maximum length of the chain is no more than 28 C, O, S and N atoms; and Z represents:

(A) an optionally substituted $(C_3-C_8)$cycloalkyl, $(C_4-C_8)$ non-aromatic cycloalkenyl, or 5 to 8 membered non-aromatic heterocyclic group, which groups may be optionally fused to a benzene ring or to a heterocyclic ring; or (B) a group of formula —$CHR_3R_4$ wherein $R_3$ and $R_4$ separately represent hydrogen; or an optionally substituted aryl, heteroaryl, $(C_3-C_8)$ cycloalkyl, $(C_4-C_8)$non-aromatic cycloalkenyl, or 5 to 8 membered non-aromatic heterocyclic group; or a group —$[Alk]_nR_a$ where Alk is an optionally substituted $(C_1-C_6)$alkyl or $(C_2-C_6)$alkenyl group optionally interrupted by one or more non-adjacent —O—, or —S— atoms or —N($R_b$)-groups [where $R_b$ is a hydrogen atom or a $(C_1-C_6)$alkyl group], n is 0 or 1, and $R_a$ is hydrogen or an optionally substituted $(C_1-C_6)$alkyl, $(C_2-C_6)$alkenyl, $(C_2-C_6)$alkynyl, aryl, heteroaryl, $(C_3-C_8)$cycloalkyl, $(C_4-C_8)$non-aromatic cycloalkenyl, or 5 to 8 membered non-aromatic heterocyclic group.

As used herein, the term "side chain of a natural or non-natural alpha amino acid" means the group R in a natural or non-natural amino acid of formula $H_2N$—CH(R)—COOH.

Examples of side chains of natural alpha amino acids include those of alanine, arginine, asparagine, aspartic acid, cysteine, cystine, glutamic acid, glycine, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Examples of side chains of non-natural alpha amino acids include:

(a) a hydrocarbon group —$CR_9R_{10}R_{11}$ in which each of $R_9$, $R_{10}$ and $R_{11}$ is independently hydrogen, $(C_1-C_6)$ alkyl, $(C_2-C_6)$alkenyl, $(C_2-C_6)$alkynyl, phenyl$(C_1-C_6)$ alkyl; or $R_9$ and $R_{10}$ together with the carbon atom to which they are attached form a 3 to 8 membered cycloalkyl or a 5- to 6-membered heterocyclic ring; or $R_9$, $R_{10}$ and $R_{11}$ together with the carbon atom to which they are attached form a tricyclic ring (for example adamantyl);

or (b) a group —$CR_{12}R_{13}R_{14}$ in which each of $R_{12}$ and $R_{13}$ is independently $(C_1-C_6)$alkyl, $(C_2-C_6)$alkenyl, $(C_2-C_6)$alkynyl, phenyl$(C_1-C_6)$alkyl, $O(C_1-C_6)$alkyl, $S(C_1-C_6)$alkyl, OH, SH, OPh, $OCH_2Ph$, SPh, $SCH_2Ph$, halogen, CN, $CO_2H$, $(C_1-C_4)$perfluoroalkyl, $CH_2OH$, $CO_2(C_1-C_6)$alkyl, or a group phenyl or heteroaryl which is optionally substituted by one or more substituents independently selected from hydrogen, hydroxyl, halogen, CN, $CO_2H$, $CO_2(C_1-C_6)$alkyl, $CONH_2$, $CONH(C_1-C_6)$alkyl, $CONH(C_1-C_6alkyl)_2$, CHO, $CH_2OH$, $(C_1-C_4)$perfluoroalkyl, $O(C_1-C_6)$alkyl, $S(C_1-C_6)$alkyl, $SO(C_1-C_6)$alkyl, $SO_2(C_1-C_6)$alkyl, $NO_2$, $NH_2$, $NH(C_1-C_6)$alkyl, $N((C_1-C_6)$alkyl$)_2$, $NHCO(C_1-C_6)$alkyl, $(C_1-C_6)$alkyl, $(C_2-C_6)$alkenyl, $(C_2-C_6)$alkynyl, $(C_3-C_8)$cycloalkyl, $C_4-C_8$) cycloalkenyl, phenyl or benzyl; and $R_{14}$ is hydrogen, OH, SH, OPh, $OCH_2Ph$, SPh, $SCH_2Ph$, halogen, CN, $CO_2H$, $(C_1-C_4)$perfluoroalkyl, $CH_2OH$, $CO_2(C_1-C_6)$ alkyl, or a group phenyl or heteroaryl which is optionally substituted by one or more substituents independently selected from hydrogen, hydroxyl, halogen, CN, $CO_2H$, $CO_2(C_1-C_6)$alkyl, $CONH_2$, $CONH(C_1-C_6)$ alkyl, $CONH(C_1-C_6alkyl)_2$, CHO, $CH_2OH$, $(C_1-C_4)$ perfluoroalkyl, $O(C_1-C_6)$alkyl, $S(C_1-C_6)$alkyl, $SO(C_1-C_6)$alkyl, $SO_2(C_1-C_6)$alkyl, $NO_2$, $NH_2$, $NH(C_1-C_6)$alkyl, $N((C_1-C_6)$alkyl$)_2$, $NHCO(C_1-C_6)$ alkyl, $(C_1-C_6)$alkyl, $(C_2-C_6)$alkenyl, $(C_2-C_6)$alkynyl, $(C_3-C_8)$cycloalkyl, $C_4-C_8$)cycloalkenyl, phenyl or benzyl; or $R_{12}$ and $R_{13}$ together with the carbon atom to which they are attached form a 3 to 8 membered cycloalkyl or a 5- to 6-membered heterocyclic ring, Functional groups in the amino acid side chains may be protected; for example carboxyl groups may be esterified (for example as a $C_1-C_6$ alkyl ester), amino groups may be converted to amides (for example as a $COC_1-C_6$ alkyl amide) or carbamates (for example as a $C(=O)OC_1-C_6$ alkyl or $C(=O)OCH_2Ph$ carbamate), hydroxyl groups may be converted to ethers (for example a $C_1-C_6$ alkyl or a $(C_1-C_6$ alkyl)phenyl ether) or esters (for example a $C(=O)$ $C_1-C_6$ alkyl ester) and thiol groups may be converted to thioethers (for example a $C_1-C_6$ alkyl thioether) or thioesters (for example a $C(=O)C_1-C_6$ alkyl thioester).

As used herein the term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

The term "cycloalkenyl" means an unsaturated alicyclic moiety having from 3–8 carbon atoms and includes, for example, cyclopropenyl, cyclobutenyl, cyclopentenyl, cyclohexenyl, cycloheptenyl and cyclooctenyl. In the case of cycloalkenyl rings of from 5–8 carbon atoms, the ring may contain more than one double bond.

The unqualified term "heterocyclyl" or "heterocyclic" refers to a 5–8 membered heterocyclic ring containing one or more heteroatoms selected from S, N and O, and optionally fused to a benzene ring, including for example, pyrrolyl, furyl, thienyl, imidazolyl; oxazolyl, thiazolyl, thiadiazolyl, pyrazolyl, pyridinyl, pyrrolidinyl, pyrimidinyl, morpholinyl, piperizinyl, indolyl, benzimidazole, maleimido, succinimido, phthalimido, 1,2-dimethyl-3,5-dioxo-1,2,4-triazolidin-4-yl, 3-methyl-2,5-dioxo-1-imidazolidinyl and 3,4,4-trimethyl-2,5-dioxo-1-imidazolidinyl, naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1, 3-dioxo-2H-pyrrolo[3,4-b]quinolin-2-yl, and 2,3-dihydro-1,3-dioxo-1H-benz[d,e]isoquinolin-2-yl The term "aryl" refers to a mono-, bi- or tri-cyclic, substituted or unsubstituted, carbocyclic aromatic group, and to groups consisting of two covalently linked substituted or unsubstituted monocyclic carbocyclic aromatic groups. Illustrative of such groups are phenyl, biphenyl and napthyl.

The term "heteroaryl" refers to a 5- or 6-membered substituted or unsubstituted aromatic ring containing one or more heteroatoms, and optionally fused to a benzyl or pyridyl ring; and to groups consisting of two covalently linked 5- or 6-membered substituted or unsubstituted aromatic rings each containing one or more heteroatoms; and to groups consisting of a substituted or unsubstituted monocyclic carbocyclic aromatic group covalently linked to a substituted or unsubstituted 5- or 6-membered aromatic rings containing one or more heteroatoms. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4-([1,2,3]-thiadiazoly-4-yl)phenyl and 5-isoxazol-3-ylthienyl.

Unless otherwise specified in the context in which it occurs, the term "substituted" as applied to any moiety herein means substituted with up to four substituents, each of which independently may be $(C_1-C_6)$alkoxy, phenoxy, hydroxy, mercapto, $(C_1-C_6)$alkylthio, amino, halo (including fluoro, chloro, bromo and iodo), trifluoromethyl, nitro, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a $(C_1-C_6)$alkyl group.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There is at least one potential chiral centre in the compounds according to the invention because of the presence of potentially asymmetric carbon atoms. The presence of several asymmetric carbon atoms gives rise to a number of diastereomers with R or S stereochemistry at each chiral centre. General formula (II), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the R$_1$ and X group =R.
but mixtures in which the above configuration predominates are also contemplated.

In the compounds of the invention:

R$_1$ may be for example hydrogen; a $(C_1-C_6)$alkyl, $(C_2-C_6)$alkenyl, phenyl, substituted phenyl, phenyl $(C_1-C_6)$alkyl, substituted phenyl$(C_1-C_6)$alkyl, heterocyclyl, substituted heterocyclyl, heterocyclyl $(C_1-C_6)$alkyl, or substituted heterocyclyl$(C_1-C_6)$alkyl group; a group BSO$_n$A— wherein n is 0, 1 or 2 and B is hydrogen or a $(C_1-C_6)$alkyl, phenyl, substituted phenyl, heterocyclyl, substituted heterocyclyl, $(C_1-C_6)$ acyl, phenacyl or substituted phenacyl group, and A represents $(C_0-C_6)$alkyl; an aryl$(C_1-C_6)$alkyl group; an amino$(C_1-C_6)$alkyl; hydroxy$(C_1-C_6)$alkyl, mercapto $(C_1-C_6)$alkyl or carboxy$(C_1-C_6)$alkyl wherein the amino-, hydroxy-, mercapto- or carboxyl-group are optionally protected or the carboxyl-group amidated; or a $(C_1-C_6)$alkyl group substituted by maleimido, succinimido, naphthalimido, 2,3-dihydro-1,3-dioxo-1H-benz[d,e]isoquinol-2-yl, carbamoyl, mono(lower alkyl)carbamoyl, di(lower alkyl)carbamoyl, di(lower alkyl)amino, carboxy-lower alkanoylamino, pyrrolidino or morpholino. Specific examples of R$_1$ groups include hydrogen, methyl, ethyl, propyl, iso-propyl, butyl, isobutyl, tert-butyl, 2,2-dimethylpropyl, cyclohexyl, phenyl, hydroxymethyl, 2-methoxyethyl, 2-methylthioethyl, 2-methylsulphonylethyl, 4-(N,N-dimethylamino)butyl, 4-(N,N-dimethylglycylamino) butyl, allyl, methoxymethyl, phenylmethyl, phthalimidomethyl, 2-phthalimidoethyl, 4-morpholinoethyl, 4-thiomorpholinoethyl, 2-methylthiazol-4-ylmethyl, tetrazol-5-ylmethyl, 6-chloropiperonyl, 1-pyrazolylmethyl, pyrid-3-ylmethyl, 1-methyl-4-imidazolylmethyl, N-methylpyrid-4-yl, 2-(pyrid-3-yloxy)ethyl, methylthiomethyl, benzylthiomethyl or thienylsulphanylmethyl. Presently preferred are compounds in which R$_1$ is hydrogen, methyl or phenylmethyl.

R$_2$ may for example be hydrogen, isobutyl, n-butyl, isopropyl, 3-methylbutyl, 1-methylpropyl, tert-butyl, n-pentyl, 3-methylbutyl, n-hexyl, n-heptyl, n-octyl, n-nonyl, n-decyl, n-undecyl, n-dodecyl, n-hexadecyl, n-tridecyl, n-tetradecyl, n-pentadecyl, n-heptadecyl, n-octadecyl, n-nonadecyl, n-eicosyl, n-heneicosyl, n-docosyl, n-tricosyi, n-tetracosyl, cyclohexyl, cyclohexylmethyl, 2-cyclohexylethyl, 3-cyclohexylpropyl, 4-cyclohexylbutyl, 5-cyclohexylpentyl, 3-methoxycarbonylpropyl, 4-methoxycarbonylbutyl, 3-carboxypropyl, 5-methoxycarbonylpentyl, 5-carboxypentyl, 2,2,2-trifluoroethyl, benzyl, 4-phenylbenzyl, 2-, 3- or 4-fluorobenzyl, 2-, 3- or 4-chlorobenzyl, 2,4-dichlorobenzyl, 4-methylbenzyl, 2-, 3- or 4-methoxybenzyl, 3,4,5-trimethoxybenzyl, 2-, 3-, or 4-ethoxybenzyl, 4-(4-methoxybenzyl)benzyl, 4-phenoxy-2-chlorobenzyl, 4-([1,2,3]-thiadiazol-4-yl) benzyl, naphthalen-2-ylmethyl, pyrid-2-, 3- or 4-ylmethyl, pyrid-2-, 3- or 4-ylethyl, piperid-2-, 3- or 4-ylmethyl, piperid-2-, 3- or 4-ylethyl, 4-tetrahydropyranylmethyl, 2-(4-morpholino)ethyl, 6-chloropiperonyl, piperon-7-yl, 2-methylthiazol-4-yl methyl, thiazol-4-ylmethyl, 2-quinolylmethyl, 2-phenylethyl, 4-phenylbutyl, 2-phenyl-1-carboxyethyl, 3-phenylpropyl, 3-morpholin-4-yl-propyl, 4-phenylbutyl, 5-phenylpentyl, tetrahydrofuran-2-ylmethyl, propyloxymethyl, propylsulphanyl, 3-methoxypropyl, 3-ethoxypropyl, 3-propoxypropyl, 3-butoxypropyl, 4-methoxybutyl, 4-ethoxybutyl, 4-propoxybutyl, 4-butoxybutyl, 5-methoxypentyl, 5-ethoxypentyl, 6-methoxyhexyl, 6-ethoxyhexyl, 13-methoxytridecyl, 3-undecyloxypropyl, 4-decyloxybutyl, 5-nonyloxypentyl, 6-octyloxyhexyl, 7-heptyloxyheptyl, 8-hexyloxyoctyl, 2-(2-methoxyethoxy)ethyl, 2-(2-methoxyethoxy(2-ethoxy)) ethyl, 3-(2-methoxyethoxy)propyl, 2-phenoxy-ethyl, 2-(4-methoxy-phenoxy)-ethyl, 3-hydroxypropyl, 4-hydroxybutyl, 5-hydroxypentyl, 6-hydroxyhexyl, 7-hydroxyheptyl, 8-hydroxyoctyl, 7,8-dihydroxyoctyl, 2-carboxyethyl, 3-carboxypropyl, 4-carboxybutyl, 6-carboxyhexyl, 7-carboxyheptyl, 8-carboxyoctyl. Presently preferred are compounds in which R$_2$ is hydrogen, n-butyl, isobutyl, 3-methylbutyl n-hexyl, n-octyl, n-nonyl, n-decyl, n-dodecyl, n-hexadecyl, benzyl, 4-chlorobenzyl, 2,4-dichlorobenzyl, 2-methoxybenzyl, 2-ethoxybenzyl 4-phenoxy-2-chlorobenzyl, 4-([1,2,3]-thiadiazoly-4-yl)benzyl, naphthalen-2-ylmethyl, 2-phenylethyl, 2-(4-morpholino)ethyl, 3-phenylpropyl, 3-methoxycarbonylpropyl, 5-methoxycarbonylpentyl, 3-carboxy-propyl, 5-carboxy-pentyl, 3-methoxypropyl, 3-ethoxypropyl, 3-butoxypropyl, 2-phenoxyethyl, 2-(4-methoxy-phenoxy)ethyl, cyclohexylmethyl or tetrahydrofuran-2-ylmethyl. Presently most preferred are compounds in which $R_2$ is isobutyl, 3-methylbutyl, n-octyl, n-nonyl, n-decyl, n-dodecyl, benzyl, 2-methoxybenzyl, 2-ethoxybenzyl, 4-chlorobenzyl, 2,4-dichlorobenzyl, 4-phenoxy-2-chlorobenzyl, 4-([1,2,3]-thiadiazoly-4-yl)benzyl, naphthalen-2-ylmethyl, 5-methoxycarbonylpentyl, 2-phenylethyl, 3-phenylpropyl,2-morpholin-4-yl-ethyl or cyclohexyl-methyl.

In compounds of the invention in which Z is not a group of formula (III) and Y is sulphonyl or carbonyl, examples of Z groups include any of those specifically listed above for $R_2$, in particular hydrogen, methyl, ethyl, n-propyl, n-butyl, n-pentyl, n-hexyl, n-heptyl, n-octyl, n-pentadecyl, n-hexadecyl, or benzyl. Presently preferred are n-hexadecyl, n-octyl, n-butyl, n-propyl, and benzyl.

In compounds of the invention in which Z is not a group of formula (III) and Y is carbonyl, examples of Z groups include include, in addition to those specified in the preceding paragraph, phenyl, 4-methylphenyl, 4-tert-butylphenyl, 3-methylphenyl, 4-chlorophenyl, 4-bromophenyl, 4-fluorophenyl, 4-trifluoromethylphenyl, 4-aminophenyl, 4-N,N-dimethylaminophenyl, 2,4,6-trimethylphenyl, 2,4,6-isopropylphenyl, 4-methoxyphenyl, 2,6-dimethoxyphenyl, 3,4-dimethoxyphenyl, 4-ethoxyphenyl, 4-n-hexyloxyphenyl, 4-n-butyloxyphenyl, 4-(2-methylbutyloxyphenyl, 4-n-heptyloxyphenyl, 4-benzyloxyoxyphenyl, 4-isopropyloxyphenyl, 4-ethoxyethoxyphenyl, 2,3-dihydrobenzofuran-5-yl, 1-napthyl, 2-napthyl, 2-thienyl or 2-acetamido-4-methyl-thiazol-5-yl, 3,5-dimethylisoxazol-5-yl, and 2,4-dimethylisoxazol-5-yl.

For compounds in which Z is a group of formula (III):

$R_5$ may for example be hydrogen or methyl. Presently preferred are compounds in which $R_5$ is hydrogen.

$R_6$ may for example be the side chain of a natural amino acid, $CH_2(C_3$–$C_8)$cycloalkyl, $C(C_1$–$C_6$ alkyl$)_3$, a 3 to 8 membered cycloalkyl substituted by $C_1$–$C_6$ alkyl or $R_{14}$ at the α-position, adamant-1-yl, $CH(Ph)_2$, $CH(C_1$–$C_4$ perfluoroalkyl$)_2$, $C(C_1$–$C_4$ perfluoroalkyl$)_3$ or $C(C_1$–$C_6$ alkyl$)_2R_{11}$, wherein $R_{11}$ is OH, SH, OPh, $OCH_2Ph$, $S(C_1$–$C_6)$alkyl, SPh, $SCH_2Ph$, halogen, $(C_1$–$C_4)$perfluoroalkyl, $CH_2OH$, $CO_2(C_1$–$C_6)$alkyl, optionally substituted phenyl or optionally substituted heteroaryl. Examples of particular $R_6$ groups include i-propyl, sec-butyl, phenylmethyl, cyclohexylmethyl, tert-butyl, 1,1-diethylprop-1-yl, 1-cyclopropylethyl, adamant-1-yl, 2-fluoroprop-2-yl, 1,1,1,3,3,3-hexafluoroprop-2-yl, 2-hydroxyprop-2-yl, 2-thioprop-2-yl, 2-methylthioprop-2-yl, 2-benzylthioprop-2-yl or 2-phenylprop-2-yl. Presently preferred are compounds in which $R_6$ is i-butyl, phenylmethyl, 2-mercapto-2-methylethyl, or t-butyl.

$R_7$ may for example be $C_1$–$C_6$ alkyl, $(C_0$–$C_4)$ perfluoroalkyl or a group D-$(C_1$–$C_6$ alkyl) wherein D represents hydroxy, $(C_1$–$C_6)$alkoxy, $(C_1$–$C_6)$alkylthio, acylamino, optionally substituted phenyl or heteroaryl. Examples of particular $R_7$ groups include methyl, ethyl, propyl, butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone)propyl, optionally substituted phenylethyl, phenylpropyl, phenylbutyl, phenylpentyl, phenyl, 2-methoxyphenyl, 3-methoxyphenyl,4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl, 3-trifluoromethylphenyl, 4-trifluoromethylphenyl, 3,5-ditrifluoromethylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, 2-napthyl, furan-2-yl, thien-2-yl, pyrrol-2-yl, tetrahydrofuran-2-yl, imidazol-2-yl, thiazol-2-yl, oxazol-2-yl, 1,2,4-ozadiazol-5-yl, 1,2,4-ozadiazol-3-yl, 1,3,4-oxadiazol-2-yl, 1,2,4-thiadiazol-5-yl, 1,3,4-thiadiazol-2-yl, pyridin-2-yl, pyridin-3-yl, pyridin-4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[b]thien-2-yl, isoxazol-5-yl or quinolin-3-yl. Presently preferred are compounds in which $R_7$ is methyl, t-butyl, phenyl, 3-pyridyl, benzyl or 2-thiazolyl.

$R_8$ may for example be hydrogen, methyl or ethyl. Presently preferred are compounds in which $R_8$ is hydrogen or methyl.

Specific compounds of the invention include those prepared according to the examples below, in particular the following:

2-[Benzyl-(octane-1-sulfonyl)-amino]-N-hydroxy-acetamide,

N-Hydroxy-2-[(2-methoxy-benzyl)-(octane-1-sulfonyl)-amino]-acetamide,

2-[(2-Ethoxy-benzyl)-(octane-1-sulfonyl)-amino]-N-Hydroxy-acetamide,

N-Hydroxy-2-[(naphthalen-2-yl-methyl)-(octane-1-sulfonyl)-amino]-acetamide,

2-[(4-Chloro-benzyl)-(octane-1-sulfonyl)-amino]-N-hydroxy-acetamide, and salts, solvates or hydrates thereof.

Compounds according to the present invention in which X is a hydroxamic acid group (—CONHHOH) may be prepared from compounds of the invention in which X is a carboxylic acid group (—COOH). That process, which forms another aspect of the invention, comprises:

(a) causing an acid of general formula (IV)

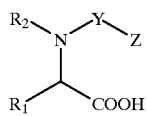

(IV)

or an activated derivative thereof to react with hydroxylamine, O-protected hydroxylamine, N,O-diprotected hydroxylamine, or a salt thereof, $R_1$, $R_2$, Y and Z being as defined in general formula (II) except that any substituents in $R_1$, $R_2$, Y and Z which are potentially reactive with hydroxylamine, O-protected hydroxylamine, N,O-diprotected hydroxylamine or their salts may themselves be protected from such reaction, then removing any protecting groups from the resultant hydroxamic acid moiety and from any protected substituents in $R_1$, $R_2$, Y and Z; or (b) deprotecting a diprotected hydroxamic acid derivative of formula (IVa)

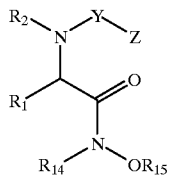

(IVa)

in which $R_1$, $R_2$, Y and Z are as defined in general formula (II), $R_{14}$ is an amino protecting group and $R_{15}$ is a hydroxyl protecting group.

For method (a) conversion of (IV) to an activated intermediate such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tert-butoxycarbonyl-O-tert-butyidimethylsilylhydroxylamine, N-tert-butoxycarbonyl-O-tetrahydropyranylhydroxylamine, and N,O-bis(tert-butoxycarbonyl)hydroxylamine.

For method (b) suitable protecting groups $R_{14}$ and $R_{15}$ are benzyl and substituted benzyl (eg 4-methoxybenzyl). Such protecting groups may be removed by hydrogenolysis, while the 4-methoxybenzyl group may also be removed by acid hydrolysis.

Compounds according to the present invention in which X is a carboxylic acid group —COOH may be prepared by a process comprising hydrolysis of a compound of formula (V):

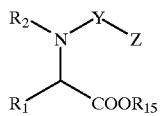

(V)

wherein $R_1$ $R_2$, Y and Z are as defined in general formula (II), and $R_{15}$ is a carboxy protecting group.

Protected carboxy groups include readily cleavable esters, such as the tert-butyl or benzyl ester.

Compounds of formula (V) wherein Y is —(S(=O)$_2$)— may be prepared by alkylation of the amino nitrogen of a sulfonamide of formula (VI) with an amine alkylating agent of formula (VII):

(VI)

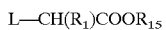

(VII)

wherein $R_1$ $R_2$, and Z are as defined in general formula (11) except that any substituents in $R_1$ $R_2$, and Z, which are potentially reactive in the alkylation reaction may themselves be protected from such reaction, $R_{15}$ is as defined for formula (V), and L is a leaving group.

Leaving groups L for the alkylation of (VI) by (VII) are well known in the art and include halogen atoms (such as bromine) and triflate.

Sulfonamides of formula (VI) may be prepared by standard methods, including the reaction of an amine of formula (VIII) with an activated sulfonic acid of formula (IX):

(VIII)

(IX)

wherein $R_2$, and Z are as defined in general formula (II). Suitable acivated derivatives of (IX) for condensation with (VII) include the sulfonyl chloride.

Compounds of formula (V) wherein Y is —(C=O)— may be prepared by acylation of an amine of formula (X) with a carboxylic acid of formula (XI) or an acylating derivative thereof:

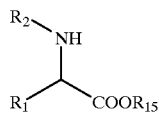

(X)

wherein $R_1$ $R_2$, and Z are as defined in general formula (II) except that any substituents in $R_1$ $R_2$, and Z, which are potentially reactive in the acylation reaction may themselves be protected from such reaction, and $R_{15}$ is as defined for formula (V).

Conditions for acylation of amines with carboxylic acids and acylating derivatives thereof are a well known in the art. Suitable activated acylating derivatives of the carboxylic acid (XI) include activated esters such as the pentafluorophenyl ester, acid anhydrides and acid halides, eg the chloride or bromide.

Compounds of formula (X) may be prepared by alkylation of an amine formula (VIII) with an amine alkylating agent of formula (VII):

 (VIII)

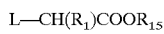 (VII)

wherein $R_1$ $R_2$, and Z are as defined in general formula (II) except that any substituents in $R_1$ $R_2$, and Z, which are potentially reactive in the alkylation reaction may themselves be protected from such reaction, $R_{15}$ is as defined for formula (V), and L is a leaving group.

Leaving groups L for the alkylation of (VIII) by (VII) are well known in the art and include halogen atoms (such as bromine) and triflate.

As mentioned above compounds of formula (II) are useful in human or veterinary medicine since they are active as inhibitors of MMPs.

Accordingly in another aspect, this invention concerns:

(i) a method of management (by which is meant treatment or prophylaxis) of diseases or conditions mediated by MMPs in mammals, in particular in humans, which method comprises administering to the mammal an effective amount of a compound as defined with respect to formula (II) above; and (ii) a compound as defined with respect to formula (II) for use in human or veterinary medicine, particularly in the management (by which is meant treatment or prophylaxis) of diseases or conditions mediated by MMPs; and (iii) the use of a compound as defined with respect to formula (II) in the preparation of an agent for the management (by which is meant treatment or prophylaxis) of diseases or conditions mediated by MMPs.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases, tumour growth, tumour angiogenisis, multiple sclerosis, psoriasis, proliferative retinopathy, neovascular glaucoma, ocular tumour, angiofibroma and hemangioma.

In a further aspect of the invention there is provided a pharmaceutical or veterinary composition comprising a compound of formula (II) together with a pharmaceutically or veterinarily acceptable excipient or carrier.

One or more compounds of general formula (II) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of the invention. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The Preparative Example which follows describes the preparation of a compound which is not part of the invention, but the process conditions and preparative techniques employed are equally applicable to the preparation of the compounds of the invention having similar structures.

Examples 1 to 30 which follow illustrate embodiments of the invention but are not intended to limit the scope in any way. The amino acids used in the examples were commercially available or were prepared according to literature procedures.

The following abbreviations have been used throughout:

| | |
|---|---|
| DIPE | Diisopropyl ether |
| DMF | N,N-Dimethylformamide |
| DMSO | Dimethytsulfoxide |
| EDC | N-Ethyl-N'-(3-dimethylaminopropyl)carbodiimide hydrochloride |
| HOBt | 1-Hydroxybenzotriazole |
| LDA | Lithium N,N-diisopropytamide |
| LHMDS | Lithium hexamethyldisilazide (lithium N,N-bis(trimethylsilyl)amide) |
| NMM | N-Methylmorpholine |
| THF | Tetrahydrofuran |
| TFA | Trifluoroacetic acid |
| TLC | Thin layer chromatography |

$^1$H and $^{13}$C NMR spectra were recorded using a Bruker AC 250E spectrometer at 250.1 and 62.9 MHz, respectively. Elemental microanalyses were performed by CHN Analysis Ltd., Alpha House, Countesthorpe Road, South Wigston, Leicester LE8 2PJ, UK or by MEDAC Ltd, Department of Chemistry, Brunel University, Uxbridge, Middlesex UB8 3PH.

Preparative Example

N-Hydroxy-2-[octyl-(toluene-4-sulfonyl)amino]-acetamide

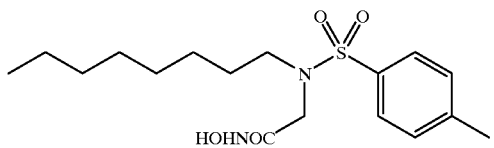

STEP A:

N-octyl-toluene-4-sulfonamide

A solution of toluene-4-sulfonyl chloride (5.0 g, 0.026 mol) in dry dichloromethane (150 ml) was cooled to 0° C. during the dropwise addition of n-octylamine (9.6 ml, 0.058 mol) with stirring over 4 minutes. The reaction mixture was then allowed to stir for 30 minutes before being diluted with dichloromethane (200 ml) and water (200 ml). The organic layer was separated and washed consecutively with 1M HCl, 0.5 M Na$_2$CO$_3$ and brine before being dried over anhydrous Na$_2$SO$_4$. The solution was filtered and concentrated in vacuo to a crude solid which was purified by flash chromatography (silica gel, 11% ethyl acetate in hexane) to give the title compound as a white solid (7.0 g, 94%). This material was then used immediately in the next step.

STEP B:

[Octyl-(toluene-4-sulfonyl)amino]-acetic acid tert-butyl ester

N-Octyl-toluene-4-sulfonamide (7.0 g, 0.025 mol) was dissolved in dry THF (200 ml) and cooled to −78° C. A 1M solution of LHMDS in THF (27.2 ml, 0.028 mol) was then added over 10 minutes. The reaction mixture was allowed to warm to −40° C. with stirring over 30 minutes. Neat tert-butyl bromoacetate (4.8 ml, 0.03 mol) was added over 5 minutes and the reaction mixture was allowed to warm to ambient temperature overnight. The reaction mixture was diluted with saturated aqueous NH$_4$Cl (200 ml) and ethyl acetate (200 ml). The organic layer was separated and washed consecutively with 1M HCl, 0.5M Na$_2$CO$_3$ and brine, dried over Na$_2$SO$_4$, filtered and concentrated in vacuo. The resulting crude oil was purified by flash chromatography (silica gel, 6% ethyl acetate in hexane) to give the title compound as a white solid (5.2 g, 53%). $^1$H NMR: δ(CDCl$_3$), 7.72 (2H, d, J=8.3 Hz), 7.27 (2H, d, J=8.4 Hz), 3.94 (2H, s), 3.23 (2H, dd, J=7.5, 7.6 Hz), 2.42 (3H, s), 1.60–1.42 (2H, m), 1.39 (9H, s), 1.34–1.17 (10H, m), 0.88 (3H, t, J=6.9 Hz).

STEP C:

[Octyl-(toluene-4-sulfonyl)amino]-acetic acid

An ice-cooled solution of [octyl-(toluene-4-sulfonyl)amino]-acetic acid tert-butyl ester (5.2 g, 0.013 mol) in dichloromethane (50 ml) was further diluted by the addition of 25% TFA in dichloromethane (200 ml). The reaction mixture was stored at 4° C. overnight. Solvents were removed under reduced pressure and the residue was azeotroped with toluene. The resulting crude oil was purified by flash chromatography (silica gel, 10% methanol in dichloromethane) to give the title compound as a white solid (4.4 g, 99%). $^1$H NMR: δ(CDCl$_3$), 9.77 (1H, br s), 7.71 2H, d, J=8.3 Hz), 7.25 (2H, d, J=8.2 Hz), 4.00 (2H, br s), 3.19 (2H, dd, J=7.4, 7.7 Hz), 2.38 (3H, s), 1.50–1.30 (2H, m), 1.30–1.05 (10H, m) and 0.85 (3H, t, J=6.6 Hz).

STEP D:

N-Benzyloxy-2-[octyl-(toluene-4-sulfonyl)amino]-acetamide

[Octyl-(toluene-4-sulfonyl)amino]-acetic acid (4.0 g, 0.012 mol) was taken up in DMF (150 ml) and treated at room temperature with NMM (1.55 ml, 0.014 mol) followed by EDC (2.92 g, 0.015 mol). The reaction mixture was allowed to stir for 15 minutes at room temperature before the addition of HOBt (2.1 g, 0.016 mol). The reaction mixture was left to stir for a further 20 minutes before a mixture of O-benzylhydroxylamine hydrochloride (1.87 g, 0.012 mol) and NMM (2.6 ml, 0.024 mol) in DMF (50 ml) was added. The reaction mixture was allowed to stir at room temperature for a further 48 h. The DMF was removed under reduced pressure and the resulting crude oil was dissolved in ethyl acetate (200 ml). The solution was washed consecutively with 1M HCl, 0.5M Na$_2$CO$_3$ and brine, dried over anhydrous Na$_2$SO$_4$, filtered and concentrated under reduced pressure. The resulting crude oil was purified by flash chromatography (silica gel, 10% methanol in dichloromethane) to give an oil which was further purified by flash chromatography (silica gel, 20% ethyl acetate in hexane) to give the title compound as a white solid (1.91 g, 37%). $^1$H NMR: δ(CDCl$_3$), 9.39 (1H, br s), 7.65 (2H, d, J=8.2 Hz), 7.45–7.20 (7H, m), 4.91 (2H, s), 3.67 (2H, br s), 3.07 (2H, dd, J=7.5, 7.9 Hz), 2.40 (3H, s), 1.50–1.33 (2H, m), 1.31–1.10 (10H, m) and 0.86 (3H, t, J=6.5 Hz).

STEP E:

N-Hydroxy-2-[octyl-(toluene-4-sulfonyl)amino]-acetamide

N-Benzyloxy-2-[octyl-(toluene-4-sulfonyl)amino]-acetamide (1.91 g, 0.0043 mol) was taken up in ethanol (150 ml), and 10% palladium on charcoal (800 mg) was added. Hydrogen gas was bubbled through the mixture for 2 hours at room temperature. The catalyst was removed by filtration and the solvent was removed under reduced pressure to give a crude solid which was purified by recrystallization from ethyl acetate/hexane (940 mg, 61%). m.p. 89° C.; $^1$H-NMR; δ(CDCl$_3$), 7.69 (2H, d, J=8.2 Hz), 7.32 (2H, d, J=8.2 Hz), 3.76 (2H, s), 3.15 (1H, d, J=7.6 Hz), 3.12 (1H, d, J=7.9 Hz), 2.43 (3H, s), 1.58–1.41 (2H, m), 1.35–1.15 (10H, m) and 0.86 (3H, t, J=6.4 Hz). $^{13}$C-NMR; δ(CDCl$_3$), 166.6, 144.2, 134.6, 129.9, 127.4, 50.7, 49.9, 31.6, 29.1, 29.0, 27.9, 26.6, 22.6, 21.5 and 14.0; IR (CDCl$_3$), ν$_{max}$ 3413, 2929, 2858, 1682, 1467, 1401, 1346, 1162 and 1091 cm$^{-1}$. Found: C, 57.27; H, 7.87; N, 7.95%; C$_{17}$H$_{28}$N$_2$O$_4$S requires C, 57.28; H, 7.92; N, 7.86%.

The compounds of the following Examples 1 to 28 were prepared according to methods described in the above Preparative Example.

EXAMPLE 1

2-[(Hexadecane-1-sulfonyl)-phenylethyl-amino]-N-hydroxy-acetamide

White solid. m.p. 110° C. $^1$H-NMR; δ(CDCl$_3$), 7.40–7.13 (5H, m), 3.87 (2H, br s), 3.56 (2H, br t, J=7.6 Hz), 2.90 (2H, br t, J=7.3 Hz), 2.80–2.68 (2H, m), 1.80–1.60 (2H, m), 1.40–1.10 (26H, m) and 0.89 (3H, t, J=6.9 Hz). $^{13}$C-NMR; δ(CDCl$_3$), 166.6, 137.9, 128.9, 128.7, 126.9, 51.9, 50.7, 48.7, 34.9, 31.9, 29.7, 29.6, 29.4, 29.1, 28.4, 23.2, 22.7 and 14.1. IR (CDCl$_3$) ν$_{max}$ 2929, 2855, 1679, 1336 and 1143 cm$^{-1}$. Found C, 64.73; H, 9.73; N, 5.79%; C$_{26}$H$_{46}$N$_2$O$_4$S requires C, 64.69; H, 9.61; N, 5.80%.

EXAMPLE 2

2-[Benzyl-(octane-1-sulfonyl)-amino]-N-hydroxy-acetamide

Oil. $^1$H-NMR; δ(CDCl$_3$), 7.40–7.20 (5H, m), 4.44 (2H, brs), 3.80 (2H, brs), 3.10 2.94 (2H, m), 1.85–1.68 (2H, m), 1.44–1.20 (10H, m) and 0.89 (3H,t, J=6.3Hz). $^1$H-NMR; δ(CDCl$_3$), 166.6, 135.0, 128.8, 128.8, 128.3, 52.8, 52.1, 47.2, 31.4, 29.0, 28.9, 28.3, 23.2, 22.5 and 14.0. IR (CDCl$_3$) ν$_{max}$ 3415, 2928, 1684, 1335 and 1144 cm$^{-1}$.

EXAMPLE 3

2-[Benzyl-(butane-1-sulfonyl)-amino]-N-hydroxy-acetamide

Golden gum. $^1$H-NMR; δ(CD$_3$OD), 7.28–7.20 (5H, m), 4.38 (2H, s), 3.62 (2H, s), 3.22–3.12 (2H, m), 1.81–1.67 (2H, m), 1.47–1.30 (2H, m) and 0.86 (3H, t, J=7.3 Hz).

EXAMPLE 4

N-Hydroxy-2-[(2-methoxy-benzyl)-(octane-1-sulfonyl)-amino]-acetamide

Yellow wax. $^1$H-NMR; δ(CD$_3$OD), 7.22 (2H, m), 6.85 (2H, m), 4.40 (2H, s), 3.73 (3H, s), 3.70 (2H, m), 3.05 (2H, m), 1.67 (2H, m), 1.40–1.08 (10H, br m) and 0.81 (3H, m).

EXAMPLE 5

2-[(2-Ethoxy-benzyl)-(octane-1-sulfonyl)-amino]-N-Hydroxy-acetamide

Yellow wax. $^1$H-NMR; δ(CD$_3$OD), 7.20 (2H, m), 6.84 (2H, m), 4.42 (2H, s), 3.95 (2H, m), 3.73 (2H, s), 3.01 (2H, m), 1.66 (2H, m), 1.36–1.07 (13H, m) and 0.79 (3H, m).

EXAMPLE 6

2-[(2,4-Dichloro-benzyl)-(octane-1-sulfonyl)-amino]-N-Hydroxy-acetamide

Yellow wax. $^1$H-NMR; δ(CD$_3$OD), 7.49 (3H, m), 4.55 (2H, s), 3.70 (2H, s), 3.15 (2H, m), 1.75 (2H, m), 1.43–1.13 (10H, m) and 0.79 (3H, m).

EXAMPLE 7

2-[(2-Chloro-4-phenoxy-benzyl)-(octane-1-sulfonyl)-amino]-N-hydroxy-acetamide

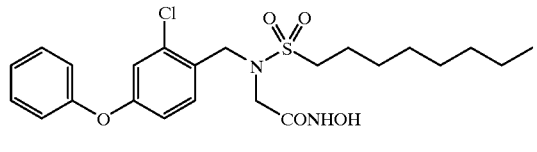

Pale yellow solid. $^1$H-NMR; δ(CD$_3$OD), 7.45–6.83 (8H, br m), 4.70 (2H, s), 3.78 (2H, s), 3.12 (2H, m), 1.65 (2H, m), 1.03–1.28 (10H, br m) and 0.78 (3H, m).

EXAMPLE 8

N-Hydroxy-2-[(octane-1-sulfonyl)-4-[1,2,3]-thiadiazol-4-yl-benzyl-amino]-acetamide

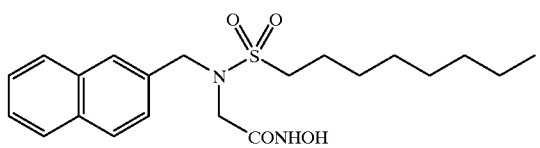

Pale yellow wax. $^1$H-NMR; δ(CD$_3$OD), 9.14 (1 H, s), 7.99 (2H, m), 7.42 (2H, m), 4.43 (2H, s), 3.68 (2H, s), 3.17 (2H, m), 1.75 (2H, m), 1.41–1.10 (10H, br m) and 0.78 (3H, m).

EXAMPLE 9

N-Hydroxy-2-[(naphthalen-2-yl-methyl)-(octane-1-sulfonyl)-amino]-acetamide

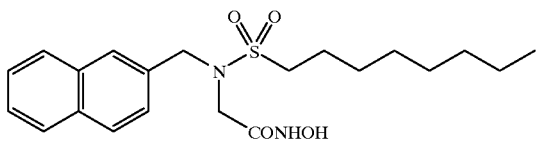

Colourless wax. $^1$H-NMR; δ(CD$_3$OD), 7.76 (3H, m), 7.49 (4H, m), 4.92 (2H, s), 3.55 (2H, s), 3.25 (2H, m), 1.79 (2H, m), 1.43–1.19 (10H, br m) and 0.82 (3H, m).

EXAMPLE 10

2-[(4-Chloro-benzyl)-(octane-1-sulfonyl)-amino]-N-hydroxy-acetamide

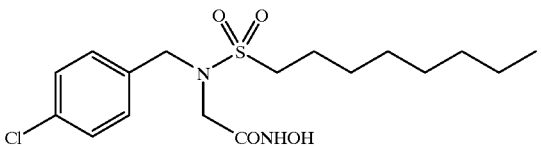

$^1$H-NMR; δ(CD$_3$OD), 7.27 (4H, m), 4.37 (2H, s), 3.62 (2H, s), 3.17 (2H, m), 1.75 (2H, m), 1.42–1.12 (10H, br m) and 0.80 (3H, m).

EXAMPLE 11

N-Hydroxy-2-[(octane-1-sulfonyl)-phenylethyl-amino]-acetamide

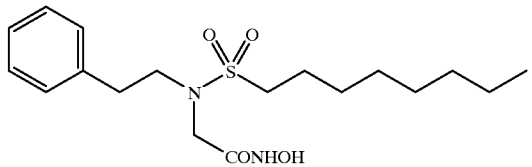

$^1$H-NMR; δ(CD$_3$OD), 7.15 (5H, m), 3.75 (2H, s), 3.41 (2H, m), 2.93 (2H, m), 2.79 (2H, m), 1.61 (2H, m), 1.20 (10H, m) and 0.78 (3H, m).

EXAMPLE 12

N-Hydroxy-2-[(3-methyl-butyl)-(octane-1-sulfonyl)-amino]-acetamide

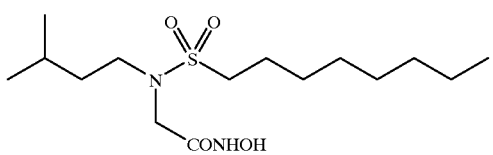

Brown wax. $^1$H-NMR; δ(CD$_3$OD), 3.76 (2H, s), 3.18–3.00 (4H, br m), 1.69 (2H, m), 1.55–1.12 (13H, br m) and 0.80 (9H, m).

EXAMPLE 13

N-Hydroxy-2-[(3-methyl-butyl)-(propane-1-sulfonyl)-amino]-acetamide

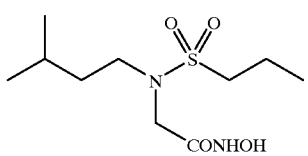

Yellow wax. $^1$H-NMR; δ(CD$_3$OD), 3.76 (2H, s) and 2.94 (2H, m). (Characteristic peaks only).

EXAMPLE 14

N-Hydroxy-2-[(3-methyl-butyl)-phenylmethanesulfonyl-amino]-acetamide

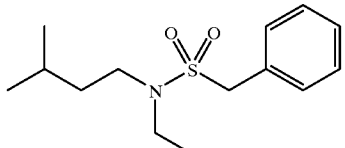

Yellow wax. $^1$H-NMR; δ(CD$_3$OD), 7.39 (2H, m), 7.26 (3H, m), 4.41 (2H, s), 3.73 (2H, s), 2.97 (2H, m), 1.59–1.09 (3H, br m) and 0.81 (6H, m).

EXAMPLE 15

2-[Cyclohexylmethyl-(octane-1-sulfonyl)-amino]-N-hydroxy-acetamide

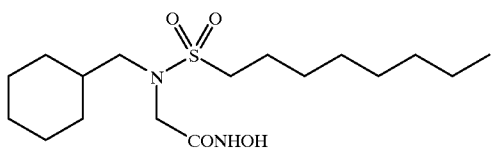

White solid. ¹H-NMR; δ(CD₃OD), 3.93–3.61 (2H, br m), 2.80 (2H, m), 2.69 (2H, m), 1.80–1.53 (10H, br m), 1.41–1.08 (10H, br m), 1.04–0.88 (3H, m) and 0.81 (3H, m).

EXAMPLE 16

2-[Cyclohexylmethyl-(propane-1-sulfonyl)-amino]-N-hydroxy-acetamide

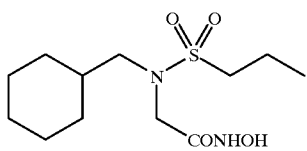

Brown wax. ¹H-NMR; δ(CD₃OD), 3.72 (2H, s), 0.95 (3H, m). (Characteristic peaks only)

EXAMPLE 17

2-[Cyclohexylmethyl-phenylmethanesulfonyl-amino]-N-hydroxy-acetamide

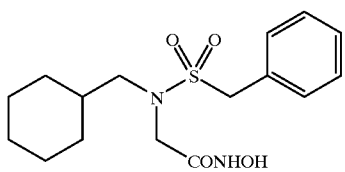

Pale yellow solid. ¹H-NMR; δ(CD₃OD), 7.32 (2H, m), 7.18 (3H, m), 4.71 (2H, s), 3.95 (2H, s), 3.10 (1H, m), 2.78 (1H, m), 1.76–1.51 (6H, br m), 1.18 (3H, m) and 0.92 (2H, m).

EXAMPLE 18

N-Hydroxy-2-[(octane-1-sulfonyl)-(3-phenyl-propyl)-amino]-acetamide

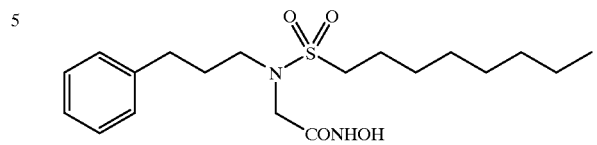

Yellow wax. ¹H-NMR; δ(CD₃OD), 7.10 (5H, m), 3.95–3.63(2H, br m), 2.96 (2H, m), 2.78–2.45 (4H, br m), 2.10–1.78 (2H, br m), 1.75–1.58 (2H, m), 1.41–1.10 (10H, br m) and 0.79 (3H, m).

EXAMPLE 19

N-Hydroxy-2-[phenylmethanesulfonyl-(3-phenyl-propyl)-amino]-acetamide

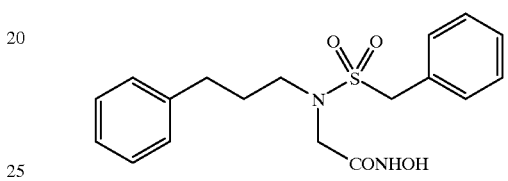

Yellow wax. ¹H-NMR; δ(CD₃OD), 7.41–7.00 (10H, br m), 3.95 (2H, s), 3.87–3.51 (2H, br m), 2.85 (2H, m), 2.56 (2H, m) and 1.86 (2H, m).

EXAMPLE 20

2-[Nonyl-(octane-1-sulfonyl)-amino]-N-hydroxy-acetamide

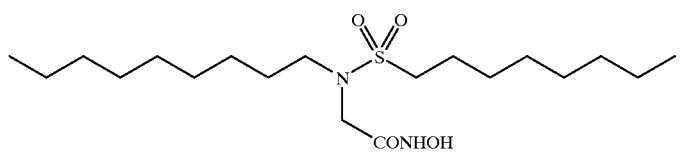

Yellow wax. ¹H-NMR; δ(CD₃OD), 3.97–3.61 (2H, br m), 2.95 (2H, m), 2.70 (2H, m), 1.76–1.53 (4H, br m), 1.41–1.05 (22H, br m) and 0.79 (6H, m).

EXAMPLE 21

2-[Nonyl-(propane-1-sulfonyl)-amino]-N-hydroxy-acetamide

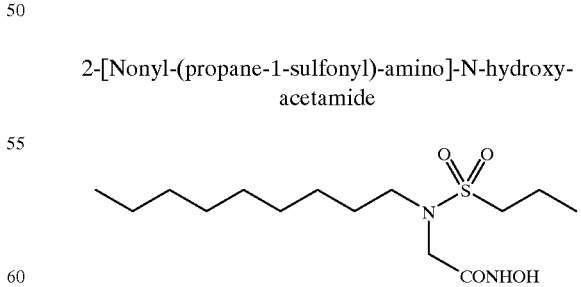

Yellow wax. ¹H-NMR: δ(CD₃OD), 3.95–3.63 (2H, br m), 2.92 (2H, m), 2.70 (2H, m), 1.75–1.52 (4H, br m), 1.43–1.11 (12H, br m) and 0.73–0.93 (6H, br m).

EXAMPLE 22

2-[Nonyl-phenylmethanesulfonyl-amino]-N-hydroxy-acetamide

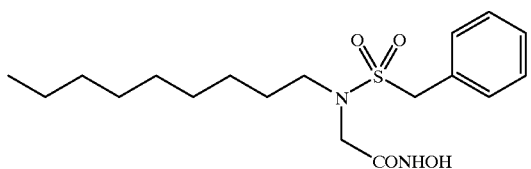

White solid; $^1$H-NMR; δ(CD$_3$OD), 7.41–7.11 (5H, br m), 3.96 (2H, s), 3.88–3.51 (2H, br m), 2.83 (2H, m), 1.55 (2H, m), 1.34–1.08 (12H, m) and 0.80 (3H, m).

EXAMPLE 23

2-[Dodecyl-(octane-1-sulfonyl)-amino]-N-hydroxy-acetamide

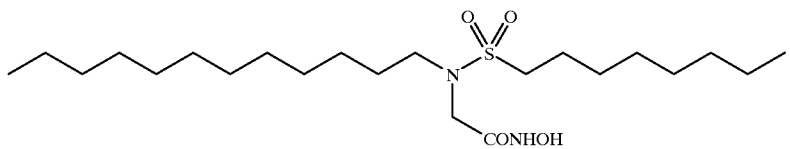

Yellow oil. $^1$H-NMR; δ(CDCl$_3$), 7.67 (1H, s), 3.92 (2H, m), 3.21 (2H, m), 1.20–1.45 (~34H, br m) and 0.83 (6H, m), $^{13}$C-NMR; δ(CDCl$_3$), 46.2, 31.9, 28.4–29.6 (several peaks), 26.6, 26.2, 22.7, 14.1 and 8.5.

EXAMPLE 24

2-[Dodecyl-phenylmethanesulfonyl-amino]-N-hydroxy-acetamide

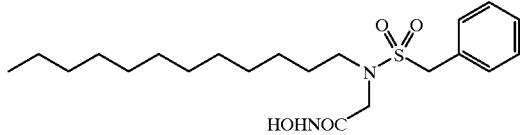

Orange oil. $^1$H-NMR; δ(CDCl$_3$), 7.36 (5H, m), 7.14 (1H, m), 6.80 (1H, d), 4.31 (2H, m), 3.62 (2H, m), 2.58 (2H, m), 1.15–1.35 (20H, m) and 0.86 (3H, t). 13C-NMR; δ(CDCl$_3$), 160.6, 130.1, 128.9, 127.2, 56.9, 49.2, 31.9, 29.5–29.3 (several peaks), 29.1, 26.5, 22.7 and 13.1.

EXAMPLE 25

6-[Hydroxycarbamoylmethyl-phenylmethanesulfonyl-amino]-hexanoic acid methyl ester (CDF)

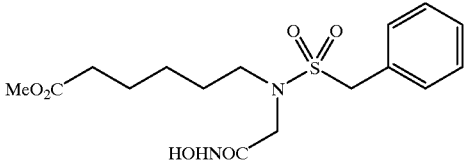

Yellow oil. $^1$H-NMR; δ(CDCl$_3$), 1.1–1.3 (4H, m), 1.5–1.7 (2H, m), 2.3 (2H, m), 3.41 (2H, m), 3.54 (2H, s), 3.57 (3H, s), 3.76 (2H, s), 6.72 (1H, d), 7.14 (1H, d), 7.34 (5H, m).

EXAMPLE 26

N-Hydroxy-2-[(2-morpholin-4-yl-ethyl)-(octane-1-sulfonyl)-amino]-acetamide

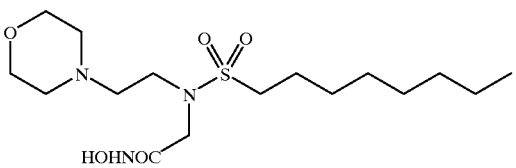

$^1$H-NMR; δ(CDCl$_3$), 9.21 (1H, s), 8.11 (1H, s), 3.96 (2H, m), 3.72 (4H, br m), 3.32 (4H, m), 3.11–3.0 (2H, m), 2.82 (1H, dt) 2.72 (1H, m), 1.85 (2H, m), 1.45–1.20 (12H, m) and 0.88 (3H, t).

EXAMPLE 27

N-Hydroxy-2-[(2-morpholino-4-yl-ethyl)-phenylmethanesulfonyl-amino]-acetamide

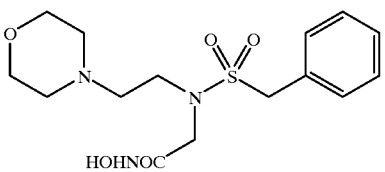

Off white solid. $^1$H-NMR; δ(CD$_3$OD), 3.42 (4H, m), 3.58 (2H, t), 3.65 (4H, m), 3.82 (2H, m), 3.93 (2H, s), 4.43 (2H, s), 7.25–7.41 (5H, m). $^{13}$C-NMR; δ(CD$_3$OD), 45.6, 52.9, 55.7, 57.1, 58.5, 65.1, 129.2, 130.0, 132.0, 134.6, 169.6.

EXAMPLE 28

2-[Decyl-phenylmethanesulfonyl-amino]-N-hydroxy-acetamide

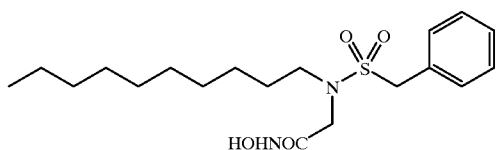

Orange oil. $^1$H-NMR; δ(CDCl$_3$), 0.87 (3H, t), 1.15–1.35 (14H, m), 2.72 (2H, m), 3.48 (2H, m), 3.92 (2H, m), 4.31 (2H, m), 6.80 (1H, d), 7.24 (5H, m), 7.81 (1H, s). $^{13}$C-NMR; δ(CDCl$_3$), 13.1, 22.7, 26.5, 29.1, 29.3–29.5 (several peaks), 31.9, 49.2, 56.9, 127.2, 128.9, 130.1, 160.6.

EXAMPLE 29

$N^4$-Hydroxycarbamoylmethyl-2,$N^4$-diisobutyl-$N^1$,$N^1$-dimethyl-succinamide

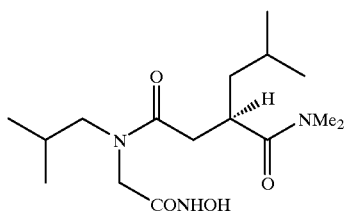

STEP A:

2R-Isobutyl-succinic acid 1-benzyl ester 4-tert-butyl ester

A solution of 2R-isobutyl-succinic acid 4-tert-butyl ester (6.50 g,. 0.028 mol) (prepared by methods described in WO 92/13831) in anhydrous DMF (100 ml) was stirred at 0° C. under an argon atmosphere during the addition of Na$_2$CO$_3$ (3.29 g, 0.034 mol) and benzyl bromide (3.70 ml, 0.031 mol). The reaction mixture was allowed to warm to ambient temperature overnight. The DMF was evaporated under reduced pressure and the residue was taken up in diethyl ether (200 ml). The solution was washed with water (100 ml), 1M HCl (100ml) and brine (100 ml), dried over anhydrous MgSO$_4$, filtered and concentrated under reduced pressure to give the title compound (8.61 g, 95%) as an oil. $^1$H NMR: δ(CDCl$_3$), 7.43–7.26 (5H, m), 5.21–5.08 (2H, m) 2.90 (1H, m), 2.62 (1H, dd, J=9.1, 16.3 Hz), 2.36 (1H, dd, J=5.4, 16.2 Hz), 1.69–1.47 (2H, br m), 1.42 (9H, s), 1.30 (1H, m), 0.92 (3H, d, J=6.4 Hz) and 0.88 (3H, d, J=6.3 Hz).

STEP B:

2R-Isobutyl-succinic acid 1-benzyl ester

An ice-cooled sample of 2R-isobutyl-succinic acid 1-benzyl ester 4-tert-butyl ester (8.55 g, 0.027 mol) was dissolved in 50% TFA in dichloromethane (50 ml). The reaction mixture was stored at 4° C. over a weekend. The solvents were removed under reduced pressure and the residue was azeotroped with toluene, dissolved in ethyl acetate (80 ml) and washed with water (100 ml). The organic phase was dried using anhydrous MgSO$_4$ and filtered. The solvent was removed under reduced pressure to give a crude oil (7.24 g, containing residual TFA) which was used without further purification. $^1$H NMR: δ(CDCl$_3$), 7.43–7.30 (5H, m), 5.15 (2H, s), 2.95(1H, m), 2.78 (1H, dd, J=9.4, 16.9 Hz), 2.49 (1H, dd, J=4.8, 16.8 Hz), 1.70–1.49 (2H, br m), 1.33 (1H, m), 0.93 (3H, d, J=6.3 Hz) and 0.89 (3H, d, J=6.3 Hz).

STEP C:

2R-(Isobutylcarbamoyl-methyl)-4-methyl-pentanoic acid benzyl ester

2R-Isobutyl-succinic acid 1-benzyl ester (7.0 g, 0.027 mol) was taken up in DMF (100 ml) and cooled to 0° C. during the addition of HOBt (4.31 g, 0.032 mol) and EDC (6.11 g, 0.032 mol). The reaction mixture was then allowed to stir at 0° C. for 30 minutes and then at ambient temperature for 2 hours. The reaction mixture was cooled to 0° C. before isobutylamine (3.89 g, 0.053 mol) was added. The reaction mixture was allowed to stir at room temperature over the weekend. The DMF was removed under reduced pressure and the resulting crude oil was taken up in dichloromethane (100 ml). The solution was washed consecutively with 1M HCl, 1M Na$_2$CO$_3$ and saturated aqueous NaCl, dried over anhydrous MgSO$_4$, filtered and the solvent was removed under reduced pressure to yield the title compound as an oil (8.41 g, 99%). $^1$H NMR: δ(CDCl$_3$), 7.49–7.27 (5H, m), 5.70 (1H, brs), 5.21–5.05 (2H, m), 3.10–2.97 (3H, br m), 2.52 (1H, dd, J=9.2, 14.6 Hz) 2.29 (1H, dd, J=5.1, 14.6 Hz), 1.66 (1H, br m), 1.61–1.50 (2H, br m), 1.32 (1H, m) and 0.97–0.82 (12H, br m).

STEP D:

2R-(Isobutylcarbamoyl-methyl)-4-methyl-pentanoic acid 2R-(Isobutylcarbamoyl-methyl)-4-methyl-pentanoic acid benzyl ester (8.30 g, 0.026 mol) was taken up in ethanol (100 ml), and 10% palladium on charcoal (1.5 g) was added. Hydrogen was bubbled through the mixture for 1 hour at room temperature. The catalyst was removed by filtration and the solvent removed under reduced pressure to give the acid (6.43 g, containing residual solvent) which was used directly in the next step. $^1$H NMR: δ(CDCl$_3$), 6.21 (1H, m), 3.14–3.02 (2H, m), 2.92 (1H, m), 2.52 (1H, dd, J=8.6, 15.1 Hz), 2.39 (1H, dd, J=4.7, 15.1 Hz), 1.77 (1H, m), 1.72–1.58 (2H, br m), 1.29 (1H, m) and 0.98–0.83 (12H, br m).

STEP E:

2R, $N^4$-Diisobutyl-$N^1$,$N^1$-dimethyl-succinamide 2R-(Isobutylcarbamoyl-methyl)-4-methyl-pentanoic acid (5.8 g, 0.025 mol) was dissolved in DMF (70 ml) and treated at 0° C. with HOBt (4.10 g, 0.030 mol) and EDC (5.82 g, 0.030 mol). The reaction mixture was allowed to stir at 0° C. for 30 minutes and then at ambient temperature for 2 h. The reaction mixture was cooled to 0° C. before addition of a 40% solution of dimethylamine in water (7.10 g, 0.063 mol). The reaction mixture was allowed to stir at room temperature over the weekend. DMF was removed under reduced pressure and the resulting crude oil was dissolved in dichloromethane (100 ml). The solution was washed consecutively with 1M HCl, 1M Na$_2$CO$_3$ and brine, dried over anhydrous MgSO$_4$, filtered and the solvent was removed under reduced pressure to yield the title compound as an oil (5.79 g, 89%). $^1$H NMR: δ(CDCl$_3$), 6.11 (1H, br s), 3.37 (1H, br m), 3.11 (3H, s), 3.06–2.97 (2H, br m), 2.93 (3H, s), 2.53 (1H, dd, J=9.9, 14.0 Hz), 2.28 (1H, dd, J=4.3, 14.0 Hz), 1.70 (1H, br m), 1.64–1.42 (2H, br m), 1.31 (1H, m) and 1.00–0.82 (12H, br m).

STEP F:

[(3R-Dimethylcarbamoyl-5-methyl-hexanoyl)-isobutyl-amino)]-acetic acid tert-butyl ester A solution of the 2R, $N^4$-diisobutyl-$N^1$,$N^1$-dimethyl-succinamide (3.85 g, 0.015 mol) in anhydrous THF (40 ml) was stirred under argon and cooled to 0° C. during the addition of a 1M solution of LHMDS in THF (16.5 m, 0.0165 mol) over 10 minutes. The reaction mixture was allowed to stir at 0° C. for 1 hour and then at ambient temperature for 1 hour, during which time the colour change was observed. The reaction mixture was cooled to 0° C. and tert butyl bromoacetate was added (6.1 ml, 0.038 mol). The reaction mixture was stirred at ambient temperature for 2 hours and then at 35° C. for 30 minutes. The reaction mixture was quenched with saturated aqueous NH$_4$Cl (40 ml) and diluted with ethyl acetate (50 ml). The organic layer was separated and washed consecutively with saturated aqueous NaHCO$_3$ (100 ml), 1M HCl (100 ml), and brine (100 ml), dried over anhydrous MgSO$_4$, filtered and the solvent was removed under reduced pressure. The resulting crude oil was purified by flash chromatography (silica gel, gradient elution with 10% to 0% hexane in ethyl acetate) to give the title compound (1.85 g, 34%) as an oil. $^1$H NMR: δ(CDCl$_3$, 2:1 mixture of rotamers), 4.22 (0.33H, d, J=18.4 Hz), 4.09 (0.66H, d, J=13.4 Hz), 3.72 (0.33H, d, J=18.4 Hz), 3.67 (0.66H, d, J=16.9 Hz), 3.38 (1H, m), 3.30–2.97 (2H, br m), 3.14 (1H, s), 3.13 (2H, s), 2.93 (2H, s), 2.91 (1H, s), 2.75 (1H, br m), 2.35 (0.66H, dd, J=4.4, 15.9 Hz), 2.20 (0.33H, dd, J=4.2, 15.6 Hz), 1.83 (1H, br m), 1.61–1.39 (2H, br m), 1.47 (3H, s), 1.44 (6H,s), 1.30 (1H, br m) and 0.98–0.79 (12H, br m).

STEP G:

N$^4$-(Hydroxycarbamoyl-methyl)-2,N$^4$-diisobutyl-N1,N$^1$-dimethyl-succinamide To an ice cooled sample of [(3R-dimethylcarbamoyl-5-methyl-hexanoyl)-isobutyl-amino)]-acetic acid tert-butyl ester (1.60 g, 0.0045 mol) was added 50% TFA in dichloromethane (10 ml). The resulting reaction mixture was stored at 4° C. overnight. The solvents were removed under reduced pressure and the residue was azeotroped with toluene, taken up in ethyl acetate (80 ml) and washed with water (100 ml). The organic phase was dried over anhydrous MgSO$_4$, filtered and the solvent was removed under reduced pressure to give the title compound as a crude oil (2.23 g, containing residual TFA) which was used without further purification. $^1$H NMR: δ(CDCl$_3$, 2:1 mixture of rotamers), 4.38–3.95 (2H, br m), 3.41 (1H, m), 3.34–3.07 (2H, br m), 3.20 (1H, s), 3.18 (2H, s), 3.02–2.74 (1H, br m), 2.99 (2H, s), 2.98 (1H, s), 2.55–2.34 (1H, br m), 1.90 (1H, br m), 1.60–1.22 (3H, br m) and 1.01–0.79 (12H, br m).

STEP H:

N$^4$-(Benzyloxycarbonyl-methyl)-2,N$^4$-dimethyl-succinamide

N$^4$-(Hydroxycarbamoyl-methyl)-2,N$^4$-diisobutyl-N$^1$,N$^1$-dimethyl-succinamide (1.30 g, 0.0041 mol) was dissolved in DMF (10 ml) and treated at 0° C. with NMM (0.56 g, 0.0041 mol) followed by EDC (0.95 g, 0.005 mol) and HOBt (0.67 g, 0.005 mol). The reaction mixture was allowed to stir at 0° C. for 20 minutes and then at ambient temperature for 2 hours before O-benzylhydroxylamine (0.76 g, 0.0062 mol) was added. The reaction mixture was allowed to stir at room temperature for a further 1.5 hours. The solvent was removed under reduced pressure and the resulting crude oil was taken up in ethyl acetate (100 ml). The solution was washed consecutively with saturated aqueous NaHCO$_3$, 1M HCl and brine, dried over anhydrous MgSO$_4$, filtered and concentrated in vacuo to a crude oil. The crude oil was purified by flash chromatography (silica gel, gradient elution with 5% to 10% methanol in dichloromethane) to give the title compound as a white solid (0.49 g, 29%). $^1$H NMR: δ(CD$_3$OD), 7.38–7.21 (5H, br m). 4.75 (2H, s), 4.11–3.65 (2H, br m), 3.25 (1H, br m), 3.17–2.97 (2H, br m), 3.07 (3H, s), 2.81 (3H, s), 2.79–2.24 (2H, br m), 1.75 (1H, br m), 1.55–1.25 (3H, br m) and 0.91–0.64 (12H, br m).

STEP I:

N$^4$-Hydroxycarbamoylmethyl-2,N$^4$-diisobutyl-N$^1$,N$^1$-dimethyl-succinamide N$^4$-(Benzyloxycarbamoyl-methyl)-2,N$^4$-diisobutyl-N', N$^1$-dimethyl-succinamide (0.45 g, 0.0011 mol) was dissolved in ethanol (5.0 ml) and 10% palladium on charcoal (100 mg) was added. Hydrogen was bubbled through the mixture for 1 hour at room temperature. The catalyst was removed by filtration and the solvent was removed under reduced pressure to give a crude solid contaminated with charcoal. The solid was then purified by column chromatography (acid-washed silica gel, 5% methanol in dichloromethane) to give the title compound as a white foamy solid (340 mg, 96%). $^1$H-NMR; δ(CDCl$_3$, 3:1 mixture of rotamers), 11.65 (0.25H, s), 10.15 (0.75H, s), 7.89 (1H, br s), 4.59 (0.75H, d, J=16.4 Hz), 4.33 (0.25H, d, J=17.8 Hz), 3.90 (0.25H, d, J=17.8 Hz), 3.66 (1H, m), 3.56 (0.75H, d, J=16.5 Hz), 3.40 (1.5H, m), 3.13 (0.75H, s), 3.11 (2.25H, s), 2.95 (2.25H, s), 2.93 (0.75H, s), 2.92 (0.5H, m), 2.79 (0.75H, m), 2.67 (0.25H, m), 2.35 (0.25H, m), 2.23 (0.75H, dd, J=4.6 Hz, 14.6 Hz), 1.92 (1H, m), 1.62 (1H, m), 1.39 (2H, m), 1.02–0.78 (12H, br m); $^{13}$C-NMR; δ(CDCl$_3$), 176.6, 176.5, 173.9, 172.5, 165.8, 56.7, 54.0, 50.0, 48.6, 40.9, 37.4, 37.3, 36.5, 35.9, 35.8, 35.0, 34.3, 31.4, 28.1, 26.6, 25.3, 23.4, 23.3, 22.4, 21.5, 21.3, 19.8 and 13.8. Found C, 56.95; H, 9.35; N, 12.34%; C$_{16}$H$_{31}$N$_3$O$_4$.0.5H$_2$O requires C 56.78%, H 9.53%, N 12.42%.

EXAMPLE 30

N$^4$-Hydroxycarbamoylmethyl-2,N$^4$-diisobutyl-N$^1$-methyl-succinamide

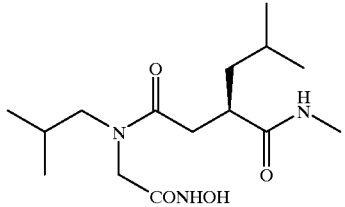

STEP A:

5-Methyl-3-methylcarbamoyl-hexanoic acid tert-butyl ester

To an ice-cooled solution of 2R-Isobutyl-succinic acid 4-tert-butyl ester (2.60 g, 11.3 mmol) in dichloromethane (25 ml) was added pentafluorophenol (2.28 g, 12.4 mmol) followed by EDC (2.38 g, 12.4 mmol). The mixture was stirred at 0° C. for 0.5 h then at room temperature for 2 h. The solution was cooled back to 0° C. and treated with methylamine (8M solution in ethanol, 3.5 ml, 28.2 mmol) and allowed to warm to room temperature then stirred for a further 2 h. The solution was washed successively with 1M Na$_2$CO$_3$ solution, 1M HCl and brine, dried over anhydrous MgSO$_4$, filtered and evaporated to leave the title compound as an oil (2.61 g, 94%). $^1$H-NMR; δ(CDCl$_3$), 5.79 (1H, br m), 2.79 (3H, d, J=4.9 Hz), 2.58 (2H, m), 2.30 (1H, m), 1.70–1.49 (2H, br m), 1.42 (9H, s), 1.17 (1H, m), 0.90 (3H, d, J=4.8 Hz) and 0.87 (3H, d, J=4.7 Hz).

STEP B:

5-Methyl-3-methylcarbamoyl-hexanoic acid

5-Methyl-3-methylcarbamoyl-hexanoic acid tert-butyl ester (2.12 g, 8.7 mmol) was deprotected by acidolysis as described in Example 30 (Step B) to provide the title compound (2.12 g, contained residual solvents). $^1$H-NMR; 5 (CDCl$_3$), 6.40 (1H, br m), 2.83 (3H, d, J=4.6 Hz), 2.70 (1H, m), 2.69 (1H, m), 2.52 (1H, m), 1.69–1.48 (2H, br m), 1.30 (1H, m), 0.92 (3H, d, J=6.5 Hz) and 0.89 (3H, d, J=6.4 Hz).

STEP C:

5-Methyl-3-methylcarbamoyl-hexanoic acid 2,3,4,5,6-pentafluorophenyl ester

To an ice-cooled solution of 5-methyl-3-methylcarbamoyl-hexanoic acid (0.40 g, 2.13 mmol) in dichloromethane (10 ml) was added pentafluorophenol (0.43 9, 2.35 mmol) and EDC (0.45 g, 2.35 mmol). The mixture was stirrred at room temperature for 2 h, diluted with more dichloromethane and washed successively with 1M $Na_2CO_3$ solution, 1M HCl and brine. The organic phase was dried (anhydrous $MgSO_4$), filtered and evaporated to leave the title compound as an oil (0.38 g, 56%), which was used in Step D without further purification. $^1$H-NMR; δ($CDCl_3$), 5.77 (1H, m), 3.10 (1H, m), 2.83 (3H, d, J=4.7 Hz), 2.75 (2H, m), 1.70 (1H, m), 1.59 (1H, m), 1.31 (1H, m), 0.95 (3H, d, J=4.9 Hz) and 0.93 (3H, d, J=4.8 Hz).

STEP D:

Isobutylamino-acetic acid benzyl ester

To an ice-cooled solution of benzyl bromoacetate (17.1 g, 74.6 mmol) in toluene (200 ml) was added isobutylamine (14.8 ml, 150 mmol) with stirring. The reaction mixture was allowed to warm to room temperature then heated at reflux for 1.5 h before leaving to cool to room temperature overnight. The solvent was removed under reduced pressure and the residue was dissolved in ethyl acetate and washed with brine. The organic phase was dried (anhydrous $MgSO_4$), filtered and evaporated to an oil which was purified further by column chromatography (silica gel, 25% ethyl acetate in hexane) to give the title compound as a yellow oil (8.96 g, 54%). $^1$H-NMR; δ($CDCl_3$), 7.35 (5H, m), 5.18 (2H, s), 3.45 (2H, s), 2.41 (2H, d, J=6.8 Hz), 1.74 (2H, m) and 0.92 (6H, d, J=6.8 Hz).

STEP E:

[Isobutyl-(5-methyl-3-methylcarbamoyl-hexanoyl)-amino]-acetic acid benzyl ester

To an ice-cooled solution of 5-methyl-3-methylcarbamoyl-hexanoic acid 2,3,4,5,6-pentafluorophenyl ester (350 mg, 0.99 mmol) in DMF (5 ml) was added isobutylamino-acetic acid benzyl ester (110 mg, 0.49 mmol) with stirring. The reaction mixture was allowed to warm to room temperature and stirred for 2 days then for 3 h at 50° C. The solvent was removed under reduced pressure, the residue was dissolved in ethyl acetate and the solution was washed successively with 1M HCl, 1M $Na_2CO_3$ and brine. The organic layer was dried ($MgSO_4$), filtered and evaporated. The residue was purified by column chromatography (silica gel, 50→100% ethyl acetate in hexane) to give the title compound as a colourless oil (130 mg, 70%). $^1$H-NMR; δ($CDCl_3$, rotamers), 7.33 (5H, m), 6.17 (1H, m), 5.15 (1H, m), 4.21 (1H, m), 3.91 (1H, m), 3.41–2.95 (2H, br m), 2.81 (2H, m), 2.75 (3H, m), 2.32 (1H, m), 1.91–1.40 (3H, br m), 1.28–1.05 (1H, m) and 0.85 (12H, m).

STEP F:

[Isobutyl-(5-methyl-3-methylcarbamoyl-hexanoyl)-amino]-acetic acid

The title compound was prepared from [isobutyl-(5-methyl-3-methylcarbamoyl-hexanoyl)-amino]-acetic acid benzyl ester (0.74 g, 1.96 mmol) by catalytic hydrogenation as described in Example 30 (Step D). White foam (0.58 g, 99%) $^1$H-NMR; δ($CDCl_3$), 4.27–3.78 (3H, br m), 3.31–2.84 (2H, br m), 2.69 (1H, m), 2.59 (3H, m), 2.77–2.26 (2H, m), 1.79 (1H, m), 1.53–1.30 (1H, m), 1.13 (1H, m) and 0.90–0.69 (12H, m).

STEP G:

$N^4$-(Benzyloxycarbamoyl-methyl)-2,$N^4$-diisobutyl-$N^1$-methyl-succinamide

The title compound was prepared from [isobutyl-(5-methyl-3-methylcarbamoyl-hexanoyl)-amino]-acetic acid (0.55 g, 1.83 mmol) by a method analogous to that described in Example 30 (Step H). The crude product was purified by column chromatography (silica gel, gradient elution 80→100% ethyl acetate in hexane). Yield: 0.34 g (46%). $^1$H-NMR; δ($CD_3OD$), 7.25 (5H, m), 4.75 (2H, m), 4.05–3.65 (2H, br m), 3.16–2.98 (2H, br m), 2.87–2.42 (2H, br m), 2.56 (3H, s), 1.75 (1H, m), 1.41 (2H, m), 1.16 (1H, m) and 0.87–0.64 (12H, m).

STEP H:

$N^4$-Hydroxycarbamoylmethyl-2,$N^4$-diisobutyl-$N^1$-methyl-succinamide $N^4$-(Benzyloxycarbamoyl-methyl)-2,$N^4$-diisobutyl-$N^1$-methyl-succinamide (0.30 g, 0.74 mmol) was deprotected by catalytic hydrogenolysis as described in Example 30 (Step 1) then purified by column chromatography (silica gel, 5% methanol in dichloromethane) to give the product as a white hygroscopic solid. m.p. 60.5–61.5° C. $^1$H-NMR; δ($CD_3OD$), 4.16–3.62 (2H, br m), 3.31–2.82 (2H, br m), 2.69 (1H, m), 2.58 (4H, m), 2.30 (1H, m), 1.82 (1H, m), 1.42 (2H, m), 1.18 (1H, m) and 0.78 (1 2H, br m). $^{13}$C-NMR; δ($CD_3OD$), 178.6, 178.4, 174.7, 174.5, 168.3, 167.9, 57.5, 55.4, 48.6, 43.1, 43.0, 42.6, 42.3, 37.0, 32.7, 28.9, 28.0, 27.0, 26.3, 23.6, 23.3, 22.6, 20.5, 20.3 and 14.4. IR (KBr) $v_{max}$ 3309, 2957, 2871, 1681, 1636, 1560 and 1490 cm$^{-1}$.

What is claimed is:

1. A compound of formula (II)

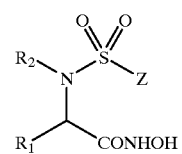

(II)

wherein $R_1$ represents hydrogen, ($C_1$–$C_6$)alkyl, ($C_2$–$C_6$)alkenyl, phenyl, substituted phenyl, phenyl($C_1$–$C_6$)alkyl, substituted phenyl($C_1$–$C_6$)alkyl, heterocyclyl, substituted heterocyclyl, heterocyclyl($C_1$–$C_6$)alkyl, or substituted heterocyclyl(($C_1$–$C_6$)alkyl group; a group $BSO_nA$— wherein n is 0, 1 or 2 and B is hydrogen or a ($C_1$–$C_6$) alkyl, phenyl, substituted phenyl, heterocyclyl, substituted heterocyclyl, ($C_1$–$C_6$)acyl, phenacyl or substituted phenacyl group, and A represents ($C_1$–$C_6$)alkyl; an aryl($C_1$–$C_6$)alkyl group; an amino($C_1$–$C_6$)alkyl; hydroxy($C_1$–$C_6$)alkyl, mercapto($C_1$–$C_6$)alkyl or carboxy($C_1$–$C_6$)alkyl wherein the amino-, hydroxy-, mercapto- or carboxyl-group are optionally protected or the carboxyl-group amidated; or a ($C_1$–$C_6$)alkyl, group substituted by maleimido, succinimido, naphthalimido, 2,3-dihydro-1,3-dioxo-1H-benz(d,e) isoquinol-2-yl, carbamoyl, mono(lower alkyl) carbamoyl, di(lower alkyl)carbamoyl, di(lower alkyl) amino, carboxy-lower alkanoylamino, pyrrolidino or morpholino.

$R_2$ represents (i) a group $Z^1$—Q—W—, or (ii) ($Z^1$—Q—W—)$_2$CH— in which each of the two groups $Z^1$—Q—W— present may be the same or different, and wherein in both cases (i) and (ii):

$Z^1$ represents hydrogen or an optionally substituted aryl, heteroaryl, non-aromatic heterocyclyl, cycloalkyl, or cycloalkenyl group, and —Q—W— taken together represent a bond, or Q represents a bond or —O— or —S— and W represents a divalent $C_1$–$C_{20}$ straight or branched alkyl or $C_2$–$C_{20}$ alkenyl group which (a) may be interrupted by one or more non-adjacent ether or thioether linkages or —N($R_x$)— groups wherein $R_x$ is hydrogen, or $C_1$–$C_6$ alkyl, and/or (b) may carry one or more substituents selected from the group consisting of —OH, —SH, —O(Alk), —S(Alk), halogen, —NH$_2$, —NH(Alk), —N(Alk)$_2$, —CO$_2$H, —CO$_2$(Alk), —CO(Alk), —CHO, —CHONH$_2$, —CONH(Alk), —CON(Alk)$_2$, —(Alk)OH, —(Alk)SH, and —NHCO(Alk) where Alk represents C$_1$–C$_6$ alkyl;

Z represents (i) a group Z$^1$—Q—W—, or (ii) (Z$^1$—Q—W—)$_2$CH— in which each of the two groups Z$^1$—Q—W— present may be the same or different, and wherein in both cases (i) and (ii):

Z$^1$ represents hydrogen or an optionally substituted aryl, heteroaryl, non-aromatic heterocyclyl, cycloalkyl, or cycloalkenyl group, and —Q—W— taken together represent a bond, or Q represents a bond or —O— or —S— and W represents a divalent C$_1$–C$_{20}$ straight or branched alkyl or C$_2$–C$_{20}$ alkenyl group which (a) may be interrupted by one or more non-adjacent ether or thioether linkages or —N(R$_x$— groups wherein R$_x$ is hydrogen, or C$_1$–C$_6$ alkyl, and/or (b) may carry one or more substituents selected from the group consisting of —OH, —SH, —O(Alk), —S(Alk), halogen, —NH$_2$, —NH(Alk), —N(Alk)$_2$, —CO$_2$H, —CO$_2$(Alk), —CO(Alk), —CHO, —CHONH$_2$, —CONH(Alk), —CON(Alk)$_2$, —(Alk)OH, —(Alk)SH, and —NHCO(Alk) where Alk represents C$_1$–C$_6$ alkyl;

provided that Z is not an aryl or heteroaryl group directly linked to the sulfur atom and at least one of Z, R$_1$, and R$_2$ contain an heteroaryl, or heterocyclic substituent;

or a salt, hydrate or solvate thereof.

2. A compound as claimed in claim 1 wherein

R$_2$ represents (i) a group Ar—Q—W— in which Ar represents optionally substituted aryl or heteroaryl, Q represents a bond or —O— or S—, and W represents a divalent C$_1$–C$_{20}$ straight or branched chain alkyl moiety which may carry one or more substituents selected from the group consisting of OH, OMe, halogen, NH$_2$, NMeH, NMe$_2$, CO$_2$H, CO$_2$Me, COMe, CHO, CONH$_2$, CONHMe, CONMe$_2$, CH$_2$OH, NHCOMe; (ii) heterocyclyl(C$_1$–C$_6$)alkyl, cycloalkyl(C$_1$–C$_6$)alkyl or cycloalkenyl(C$_1$–C$_6$)alkyl group; or (iii) a linear saturated or unsaturated C$_2$–C$_{20}$ hydrocarbon chain, which chain (a) may be interrupted by one or more non-adjacent —O— or —S— atoms or —N(R$_x$) groups wherein R$_x$ is hydrogen, methyl or ethyl, and/or (b) may be substituted with one or more groups selected from (C$_1$–C$_6$)alkyl, OH, OMe, halogen, NH$_2$, NMeH, NMe$_2$, CO$_2$H, CO$_2$Me, COMe, CHO, CONH$_2$, CONHMe, CONMe$_2$, CH$_2$OH, NHCOMe, provided that the maximum length of the chain is no more than 28 C, O, S and N atoms; and Z represents:

(A) an optionally substituted (C$_3$–C$_8$)cycloalkyl, (C$_4$–C$_8$)non-aromatic cycloalkenyl, or 5 to 8 membered non-aromatic heterocyclic group; or (B) a group of formula —CHR$_3$R$_4$ wherein R$_3$ and R$_4$ separately represent hydrogen; or an optionally substituted aryl, heteroaryl, (C$_3$–C$_8$) cycloalkyl, (C$_4$–C$_8$) non-aromatic cycloalkenyl, or 5 to 8 membered non-aromatic heterocyclic group; or a group —(Alk)$_n$R$_a$ where Alk is an optionally substituted (C$_1$–C$_6$)alkyl or (C$_2$–C$_6$)alkenyl group optionally interrupted by one or more non-adjacent —O—, or —S— atoms or —N(R$_b$)-groups where R$_b$ is a hydrogen atom or a (C$_1$–C$_6$)alkyl group, n is 0 or 1, and R$_a$ is (i) hydrogen or (ii) an optionally substituted (C$_1$–C$_{17}$)alkyl or (C$_2$–C$_{17}$)alkenyl group optionally interrupted by one or more non-adjacent —O—, or —S— atoms or —N(R$_b$)-groups where R$_b$ is a hydrogen atom or a (C$_1$–C$_6$)alkyl group or (iii) an optionally substituted aryl, heteroaryl, (C$_3$–C$_8$) cycloalkyl, (C$_4$–C$_8$)non-aromatic cycloalkenyl, or 5 to 8 membered non-aromatic heterocyclic group.

3. A compound as claimed in claim 1 wherein

R$_2$ represents a phenyl (C$_1$–C$_6$)alkyl, heterocyclyl (C$_1$–C$_6$)alkyl, cycloalkyl(C$_1$–C$_6$)alkyl or cycloalkenyl (C$_1$–C$_6$)alkyl group, or a linear saturated or unsaturated C$_2$–C$_{20}$ hydrocarbon chain, which chain (a) may be interrupted by one or more non-adjacent —O— or —S— atoms or N(R$_x$)-groups wherein R$_x$ is hydrogen, methyl or ethyl, and/or (b) may be substituted with one or more groups selected from (C$_1$–C$_6$)alkyl, OH, OMe, halogen, NH$_2$, NMeH, NMe$_2$, CO$_2$H, CO$_2$Me, COMe, CHO, CONH$_2$, CONHMe, CONMe$_2$, CH$_2$OH, NHCOMe;

provided that the maximum length of the chain is no more than 28 C, O, S and N atoms; and Z represents:

(A) an optionally substituted (C$_3$–C$_8$)cycloalkyl, (C$_4$–C$_8$)non-aromatic cycloalkenyl, or 5 to 8 membered non-aromatic heterocyclic group; or (B) a group of formula —CHR$_3$R$_4$ wherein R$_3$ and R$_4$ separately represent hydrogen; or an optionally substituted aryl, heteroaryl, (C$_3$–C$_8$) cycloalkyl, (C$_4$–C$_8$)non-aromatic cycloalkenyl, or 5 to 8 membered non-aromatic heterocyclic group; or a group —(Alk)$_n$R$_a$ where Alk is an optionally substituted (C$_1$–C$_6$)alkyl or (C$_2$–C$_6$)alkenyl group optionally interrupted by one or more non-adjacent —O—, or —S— atoms or —N(R$_b$)-groups where R$_b$ is a hydrogen atom or a (C$_1$–C$_6$) alkyl group, n is 0 or 1, and R$_a$ is hydrogen or an optionally substituted (C$_1$–C$_6$alkyl or (C$_2$–C$_6$) alkenyl, aryl, heteroaryl, (C$_3$–C$_8$)cycloalkyl, (C$_4$–C$_8$)non-aromatic cycloalkenyl, or 5 to 8 membered non-aromatic heterocyclic group.

4. A compound as claimed in any one of claim 1 to 3 wherein R$_1$ is methyl, ethyl, propyl, iso-propyl, butyl, isobutyl, tert-butyl, 2,2-dimethylpropyl, cyclohexyl, phenyl, hydroxymethyl, 2-methoxyethyl, 2-methylthioethyl, 2-methylsulphonylethyl, 4-(N,N-dimethylamino)butyl, 4-(N,N-dimethylglycylamino)butyl, allyl, methoxymethyl, phenylmethyl, phthalimidomethyl, 2-phthalimidoethyl, 4-morpholinoethyl, 4-thiomorpholinoethyl, 2-methylthiazol-4-ylmethyl, tetrazol-5-ylmethyl, 6-chloropiperonyl, 1-pyrazolylmethyl, pyrid-3-ylmethyl, 1-methyl-4-imidazolylmethyl, N-methylpyrid-4-yl, 2-(pyrid-3-yloxy)ethyl, methylthiomethyl, benzylthioethyl or thienylsulphanylmethyl.

5. A compound as claimed in any one of claims 1 to 3 wherein R$_1$ is hydrogen.

6. A compound as claimed in any one of claims 1 to 3 wherein R$_2$ is hydrogen, isobutyl, n-butyl, isopropyl, 3-methylbutyl, 1-methylpropyl, tert-butyl, n-pentyl, 3-methylbutyl, n-hexyl, n-heptyl, n-octyl, n-nonyl, n-decyl, n-undecyl, n-dodecyl, n-hexadecyl, n-tridecyl, n-tetradecyl, n-pentadecyl, n-heptadecyl, n-octadecyl, n-nonadecyl, n-eicosyl, cyclohexyl, cyclohexylmethyl, 2-cyclohexylethyl, 3-cyclohexylpropyl, 4-cyclohexylbutyl, 5-cyclohexylpentyl, 3-methoxycarbonylpropyl, 4-methoxycarbonylbutyl, 3-carboxypropyl, 5-methoxycarbonylpentyl, 5-carboxypentyl, 2,2,2-trifluoroethyl, benzyl, 4-phenylbenzyl, 2-, 3- or 4-fluorobenzyl, 2-, 3- or 4-chlorobenzyl, 2,4-dichlorobenzyl, 4-methylbenzyl, 2-, 3- or 4-methoxybenzyl, 3,4,5-trimethoxybenzyl, 2-, 3-, or 4-ethoxybenzyl, 4-phenoxy-2-chlorobenzyl, naphthalen-2-ylmethyl, pyrid-2-, 3- or 4-ylmethyl, pyrid-2-, 3- or 4-ylethyl, piperid-2-, 3- or 4-ylmethyl, piperid-2-, 3- or 4-ylethyl, 4-tetrahydropyranylmethyl, 2-(4-morpholino)ethyl, 6-chloropiperonyl, piperon-7-yl, 2-methylthiazol-4-ylmethyl, thiazol-4-ylmethyl, 2-quinolylmethyl, 2-phenylethyl, 4-phenylbutyl, 2-phenyl-1-carboxy-ethyl, 3-phenylpropyl, 3-morpholin-4-yl-propyl, 4-phenylbutyl, 5-phenylpentyl, tetrahydrofuran-2-ylmethyl, propyloxymethyl, 3-methoxypropyl, 3-ethoxypropyl, 3-propoxypropyl, 3-butoxypropyl, 4-methoxybutyl, 4-ethoxybutyl, 4-propoxybutyl, 4-butoxybutyl, 5-methoxypentyl, 5-ethoxypentyl, 6-methoxyhexyl, 6-ethoxyhexyl, 13-methoxytridecyl, 3-undecyloxypropyl, 4-decyloxybutyl, 5-nonyloxypentyl, 6-octyloxyhexyl, 7-heptyloxylheptyl, 8-hexyloxyoctyl, 2-(2-methoxyethoxy)ethyl, 2-(2-methoxyethoxy(2-ethoxy))ethyl, 3-(2-methoxyethoxy)propyl, 2-phenoxy-ethyl, 2-(4-methoxyphenoxy)-ethyl, 3-hydroxypropyl, 4-hydroxybutyl, 5-hydroxypentyl, 6-hydroxyhexyl, 7-hydroxyheptyl, 8-hydroxyoctyl, 7,8-dihydroxyactyl, 2-carboxyethyl, 3-carboxypropyl, 4-carboxybutyl, 6-carboxyhexyl, 7-carboxyheptyl, or 8-carboxyoctyl.

7. A compound as claimed in any one of claims 1 to 3 wherein $R_2$ is hydrogen, n-butyl, isobutyl, 3-methylbutyl n-hexyl, n-octyl, n-nonyl, n-decyl, n-dodecyl, n-hexadecyl, benzyl, 4-chlorobenzyl, 2,4-dichlorobenzyl, 2-methoxybenzyl, 2-ethoxybenzyl 4-phenoxy-2-chlorobenzyl, 4-((1,2,3)-thiadiazoly-4-yl)benzyl, naphthalen-2-ylmethyl, 2-phenylethyl, 2-(4-morpholino)ethyl, 3-phenylpropyl, 3-methoxycarbonylpropyl, 5-methoxycarbonylpentyl, 3-carboxy-propyl, 5-carboxypentyl, 3-methoxypropyl, 3-ethoxypropyl, 3-butoxypropyl, 2-phenoxyethyl, 2-(4methoxyphenoxy) ethyl, cyclohexylmethyl or tetrahydrofuran-2-ylmethyl.

8. A compound as claimed in any one of claims 1 to 3 to wherein $R_2$ is isobutyl, 3-methylbutyl, n-octyl, n-nonyl, n-decyl, n-dodecyl, benzyl, 2-methoxybenzyl, 2-ethoxybenzyl, 4-chlorobenzyl, 2,4-dichlorobenzyl, 4-phenoxy-2-chlorobenzyl, 4-((1,2,3)-thiadiazoly-4-yl) benzyl, naphthalen-2-ylmethyl, 5-methoxycarbonylpentyl, 2-phenylethyl, 3-phenylpropyl,2-morpholin-4-yl-ethyl or cyclohexylmethyl.

9. A compound as claimed in any one of claims 1 to 3 wherein Z is methyl, ethyl, n-propyl, n-butyl, n-pentyl, n-hexyl, n-heptyl, n-octyl, n-pentadecyl, n-hexadecyl, or benzyl.

10. A pharmaceutical composition comprising a compound as claimed in any one of claims 1 to 3 and a pharmaceutically acceptable carrier therefor.

* * * * *